(12) United States Patent
Yoo

(10) Patent No.: US 8,480,980 B2
(45) Date of Patent: Jul. 9, 2013

(54) THIN FILM BIO VALVE DEVICE AND ITS CONTROLLING APPARATUS

(75) Inventor: Jae Chern Yoo, Gwacheon-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 323 days.

(21) Appl. No.: 12/747,117

(22) PCT Filed: Dec. 10, 2008

(86) PCT No.: PCT/KR2008/007280
§ 371 (c)(1),
(2), (4) Date: Jun. 9, 2010

(87) PCT Pub. No.: WO2009/075513
PCT Pub. Date: Jun. 18, 2009

(65) Prior Publication Data
US 2010/0288949 A1      Nov. 18, 2010

(30) Foreign Application Priority Data

Dec. 10, 2007   (KR) .................. 10-2007-0128592

(51) Int. Cl.
*B01L 99/00*   (2010.01)

(52) U.S. Cl.
USPC ............ 422/537; 422/50; 422/540; 422/500; 422/501; 422/502; 436/180

(58) Field of Classification Search
USPC ..... 422/50, 500–502, 536, 537, 540; 436/180
See application file for complete search history.

(56) References Cited

U.S. PATENT DOCUMENTS
2004/0155213 A1 *   8/2004   Yoo .................................. 251/65

FOREIGN PATENT DOCUMENTS
| KR | 10-2004-0004014 A | 1/2004 |
| KR | 10-2005-0014797 A | 2/2005 |
| KR | 10-0639816 B1 | 11/2006 |
| WO | 2006/118420 A1 | 11/2006 |
| WO | 2007/001160 A1 | 1/2007 |

* cited by examiner

*Primary Examiner* — Jyoti Nagpaul
(74) *Attorney, Agent, or Firm* — Sughrue Mion, PLLC

(57) ABSTRACT

A thin film bio valve device and an apparatus for controlling the thin film bio valve device are effectively applied in a valve structure of a thin film device, such as a lab-on-a-chip, a protein chip, or a DNA chip, for diagnosing and/or detecting a small amount of material in a fluid.

41 Claims, 30 Drawing Sheets

FIG. 4
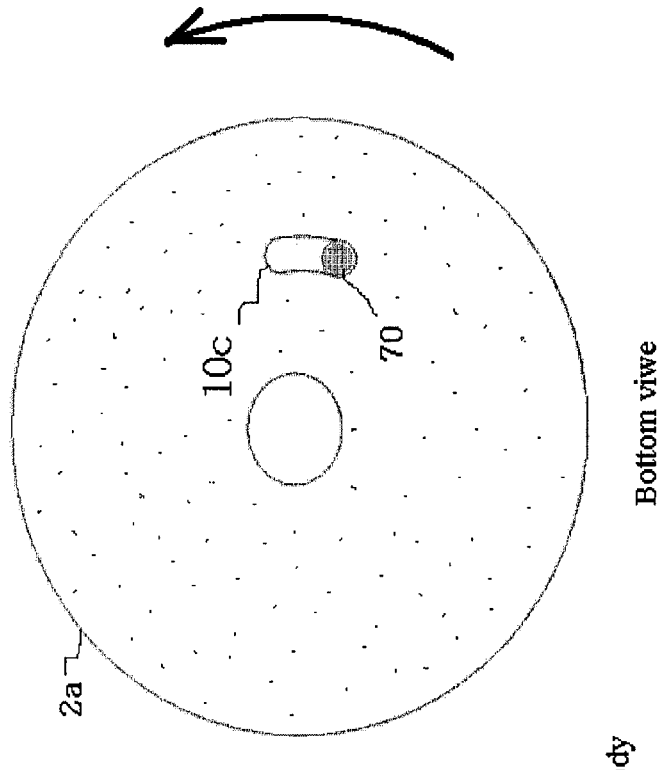
Bottom view
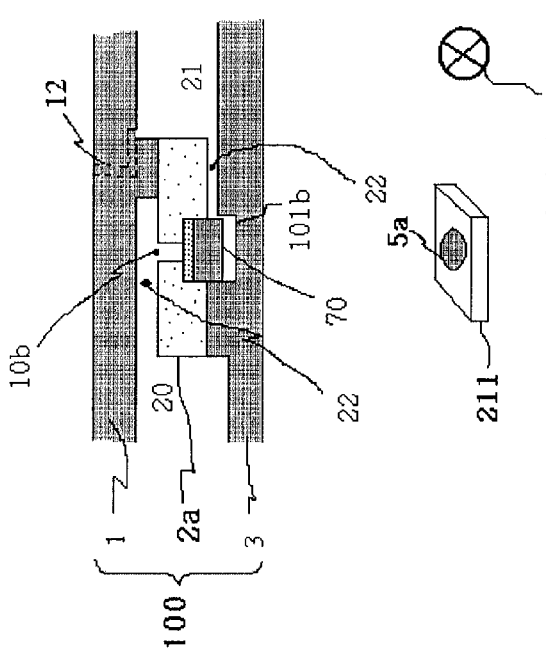
counter-clockwise rotation of the body

FIG. 5
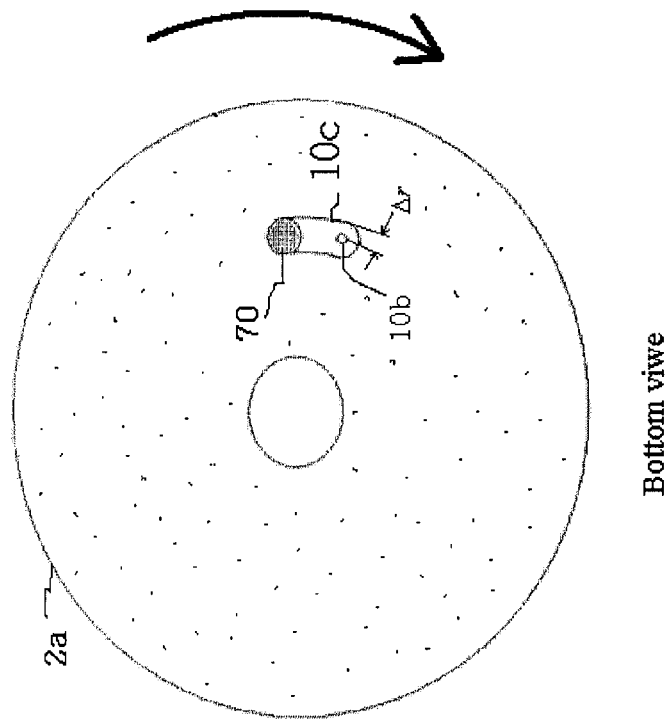
Bottom viwe
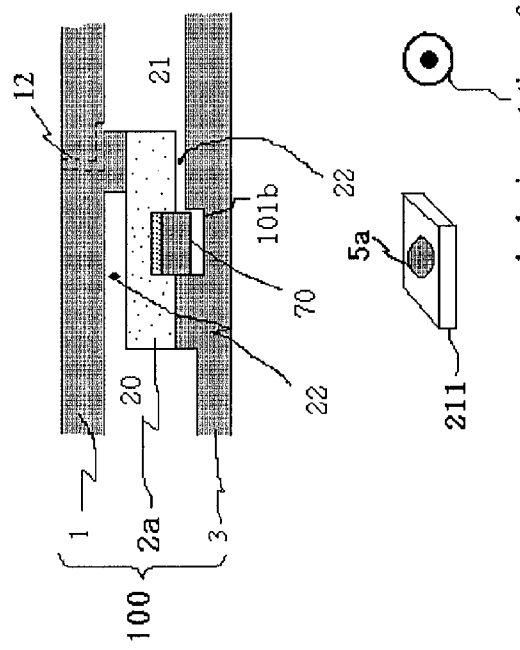
clockwise rotation of the body

FIG. 7
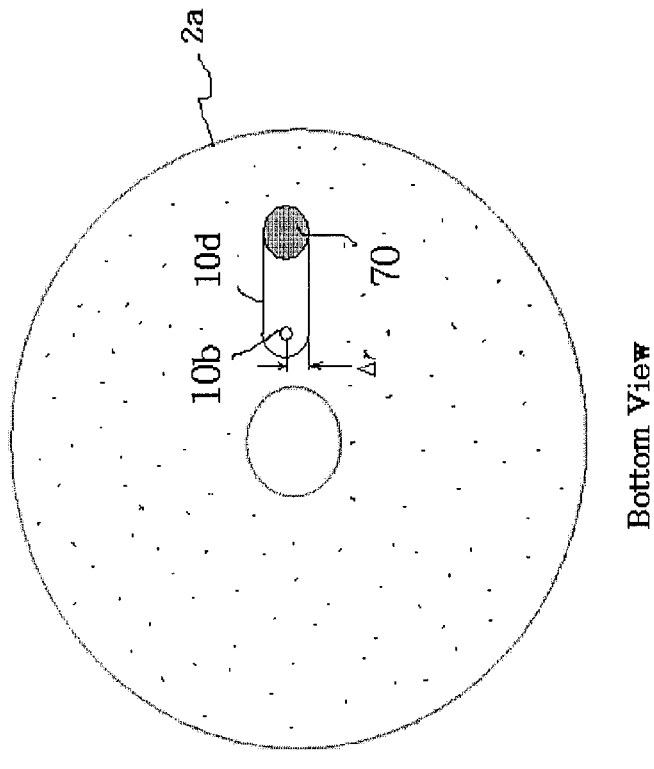
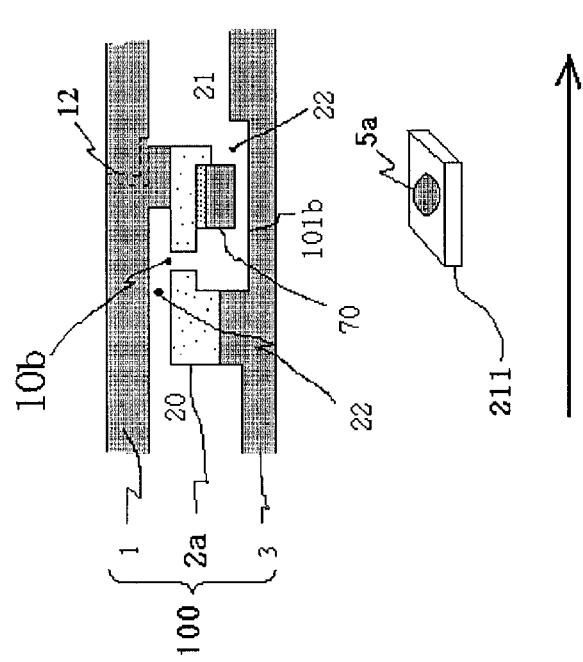

FIG. 12
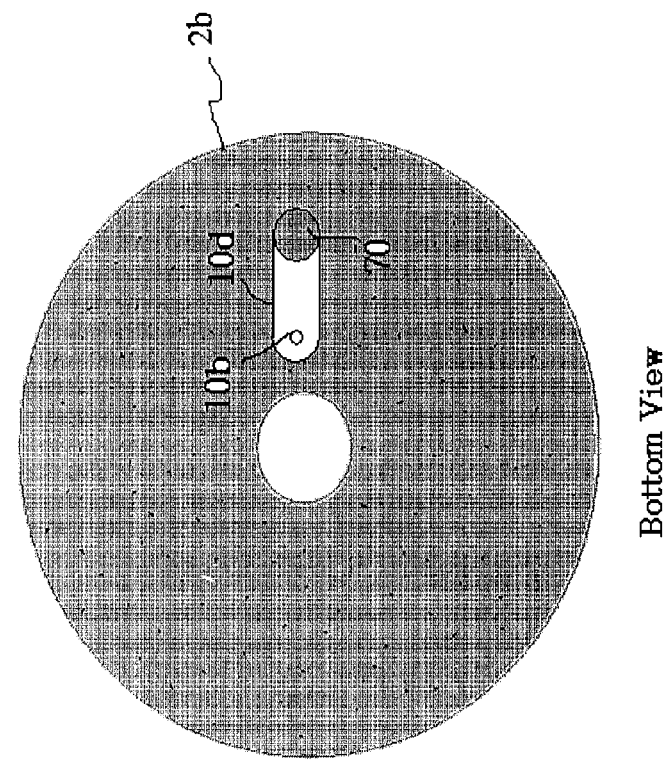
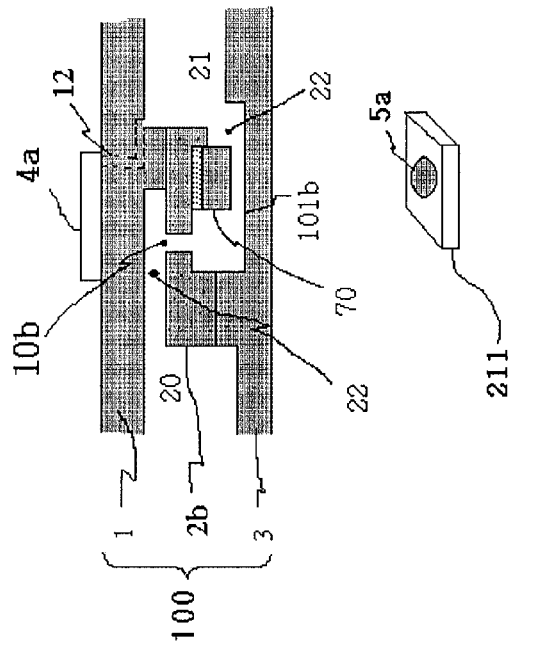

FIG. 14
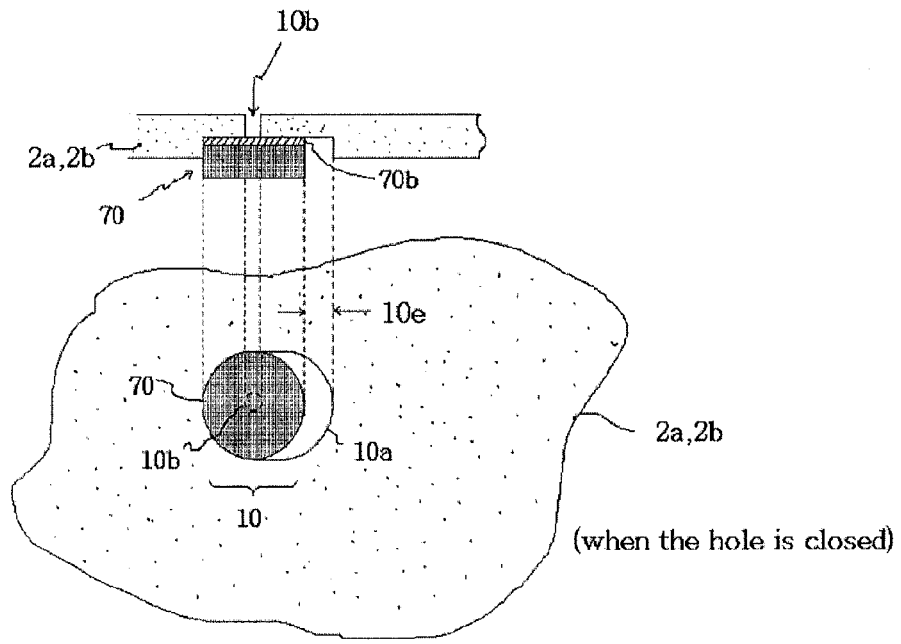
(when the hole is closed)
the direction of the centrifugal force
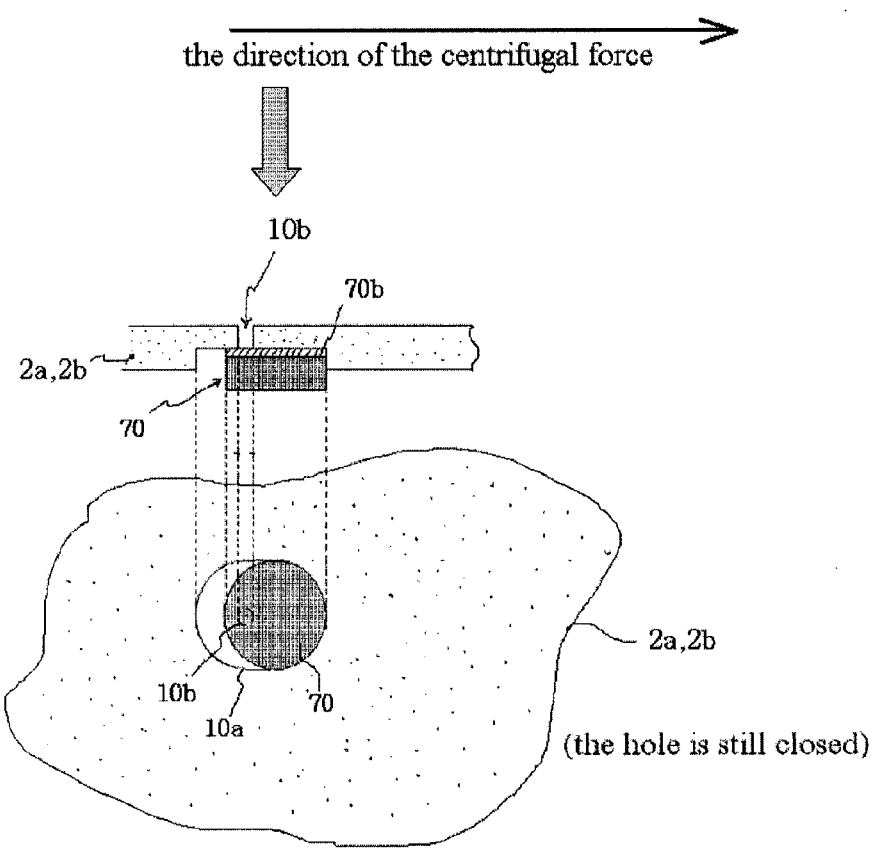
(the hole is still closed)

FIG. 19
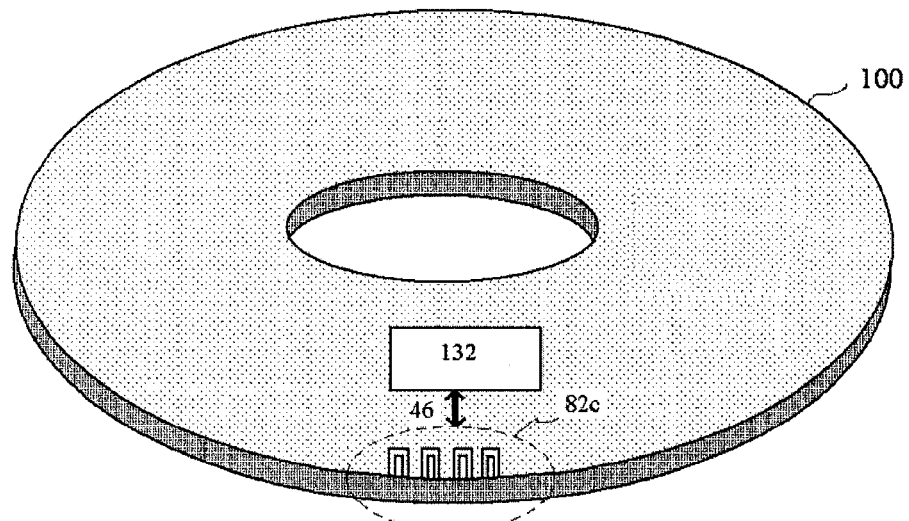
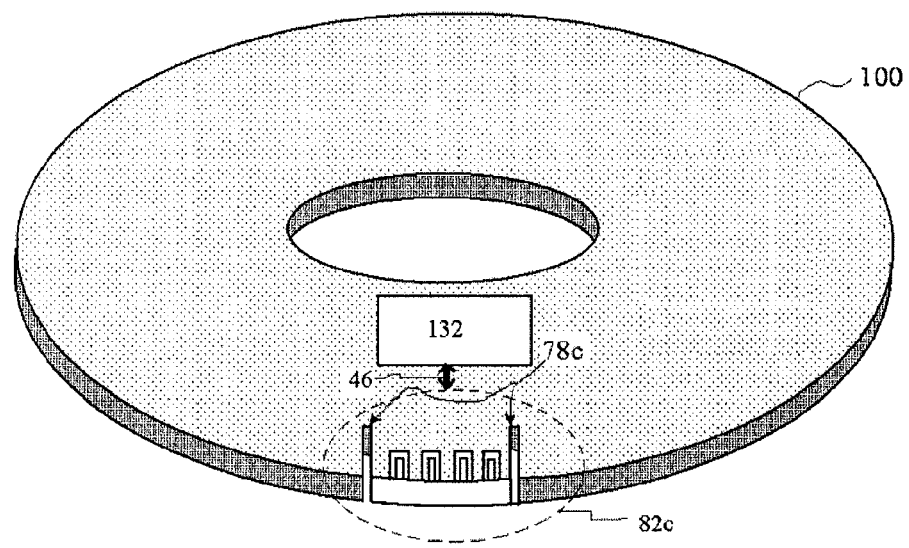
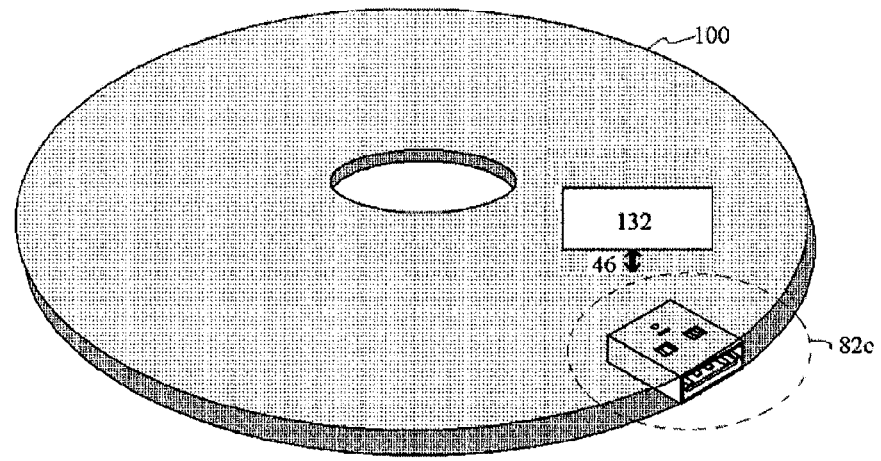

FIG. 22
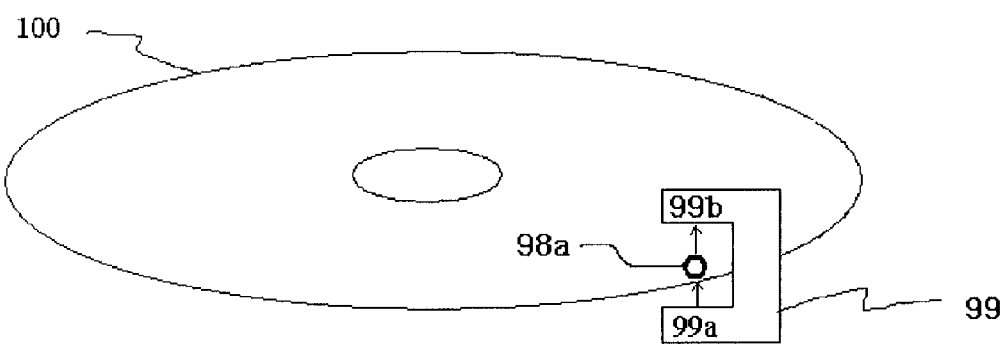
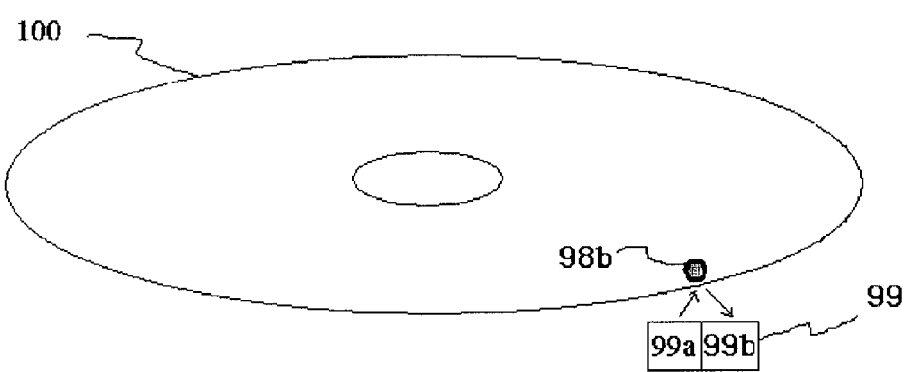

THIN FILM BIO VALVE DEVICE AND ITS CONTROLLING APPARATUS

TECHNICAL FIELD

The inventive concept relates to a control of the flow and/or amount of a fluid in an assay device for diagnosing and/or detecting a small amount of a biomaterial included in a fluid.

More particularly, the inventive concept relates to a thin film bio valve device for controlling the flow and/or amount of a fluid and an apparatus for controlling the thin film bio valve device. The thin film bio valve device includes a channel hole and the channel hole is closed or opened by using various methods. For example, a body of the thin film bio valve device includes a magnetic valve that moves due to a magnetic force formed between a fixed top permanent magnet disposed above a channel hole and a movable permanent magnet disposed under the channel hole and thus, when the magnetic valve moves in a clockwise or counter-clockwise direction, the channel hole is opened or closed.

In another example, a body of the thin film bio valve device includes a magnetic valve and the magnetic valve is reversibly moved in a radial direction due to a magnetic force formed between a fixed top permanent magnet disposed above a channel hole and a movable permanent magnet disposed under the body in order to open or close the channel hole.

In another example, a body of the thin film bio valve device includes a magnetic valve and an intermediate substrate formed of a ferromagnetic material, wherein a channel hole is closed due to an attractive force between the magnetic valve and the intermediate substrate and then, the magnetic valve is moved in a clockwise or counter-clockwise direction due to a magnetic force formed between a movable permanent magnet disposed under the channel hole and the magnetic valve, thereby opening or closing the channel hole.

In another example, a body of the thin film bio valve device includes a magnetic valve and an intermediate substrate formed of a ferromagnetic material, wherein a channel hole is closed due to an attractive force between the magnetic valve and the intermediate substrate and then, the magnetic valve is reversibly moved in a radial direction due to a magnetic force formed between a movable permanent magnet disposed under the channel hole and the magnetic valve, thereby opening or closing the channel hole.

In another example, a body of the thin film bio valve device includes a magnetic valve and an intermediate substrate formed of a ferromagnetic material, wherein a channel hole is closed due to an attractive force between the magnetic valve and the intermediate substrate and the channel hole is opened due to a magnetic force formed between a movable permanent magnet disposed under the channel hole and the magnetic valve.

A thin film bio valve device and an apparatus for controlling the thin film bio valve device according to embodiments of the inventive concept are used in a thin film device for diagnosing and/or detecting a small amount of biomaterial in a fluid. Examples of the thin film device include a lab-on-a-chip, a protein chip, and a DNA chip. In addition, a thin film bio valve device and an apparatus for controlling the thin film bio valve device according to embodiments of the inventive concept may constitute a micro valve apparatus for opening and closing a channel hole formed in a thin film body by modifying a conventional disk such as a CD-ROM or DVD.

BACKGROUND ART

For most clinical diagnosis assay devices for detecting a small amount of sample, multiple sample preparation and automatic reagent addition devices have been developed and a device having a parallel or series structure can assay many test samples, in order to increase efficiency and economic efficiency. Usually, such automatic reagent preparation devices and automatic assay devices are integrated in a single thin film device. Such a thin film device for clinical trials is used to automatically or manually perform hundreds of assays by using a small amount of sample and reagent within one hour. Thin film devices for clinical trials necessarily include valves for automatically loading the sample and/or reagent, such as an enzyme or a buffer solution. However, designing valves are complex and thus forming thin-film devices including such valves is difficult. Accordingly, to overcome these problems, a simple valve that is appropriate for thin-films is needed to be developed.

A standard compact disc is formed by using a 12 cm-polycarbonate substrate, a reflective metal layer, and a protective lacquer coating method. The format of DVDs, CDs, and CD-ROMs is described in the ISO 9660 industrial standard. The polycarbonate substrate may be formed of transparent polycarbonate having an optical quality. A portion of the polycarbonate substrate constitutes a data layer of the DVD or CD and data is stored in the data layer in a series of pits formed by engraving with a stamper in an injection molding process. Generally, a stamping master is formed of glass. The polycarbonate substrate can be modified into a thin film assay device, such as a bio disk, for diagnosing and detecting a small amount of material in a fluid. In this case, in the injection molding process, on a surface of a disk, a channel through which a fluid flows and a chamber in which a buffer solution is to be contained are formed instead of pits. Accordingly, a thin film valve can be needed to smoothly control the flow and/or amount of a fluid flowing through the channel formed in the thin film assay device.

Hereinafter, a disk in which a bio chip, such as a lab-on-a-chip, a protein chip, or a DNA chip, for diagnosing and detecting a small amount of a bio material in a fluid, which is formed by modifying a conventional disk, such as CD-ROM or DVD, and a thin film valve are integrated together; or a disk for performing a bio and chemical process to diagnose and detect a small amount of a bio material in a fluid by integrating a thin film valve will be referred to as a "bio disk" or "thin film bio valve device".

A device for assaying a fluid by using a centrifugal force of a specimen loaded through an inlet of a disk has been developed. In addition, a device for separating a specimen loaded through an inlet of a disk by moving the specimen to a channel and a chamber due to a centrifugal force has been developed. However, for these devices, it is difficult to manufacture valves having a thin film structure and thus, the amount of the fluid cannot be accurately controlled.

In general, known valves using an electromagnet open or close a channel by using a cylinder or plunger that moves due to a magnetic force. However, to obtain sufficient magnetic force to move the cylinder or plunger, a suitably sized ferrite core and many coils to be wound thereon are needed, and a large amount of electricity may also be needed when valves are on and off to move the cylinder and plunger. Thus, these valves using an electromagnet cannot be manufactured to have a thin film structure due to the size of the electromagnet. In addition, since heat is generated due to high power consumption, unique properties of a fluid may be changed, which is a problem for diagnosing and/or detecting a small amount of material in a fluid. These valves using an electromagnet are known. To overcome these problems, an embodiment of the inventive concept uses, instead of an electromagnet, a magnetic valve and a movable permanent magnet to open or close the channel hole. Thus, in this case, electricity for generating a magnetic force is not needed and heat is not generated, and thus unique properties of a fluid are not changed.

A thin film bio valve device according to an embodiment of the inventive concept enables formation of a super-thin-film valve and integration of many valves in a unit area. Accordingly, the thin film bio valve device according to an embodiment of the inventive concept may constitute a valve structure of a thin film device, such as a lap-on-a-chip or a DNA chip, for diagnosing and/or detecting a small amount of a material included in a fluid.

For example, the thin film bio valve device according to an embodiment of the inventive concept may constitute a micro valve apparatus for opening and closing a channel hole formed in a thin film body by modifying a conventional disk such as a CD-ROM or DVD, or controlling the amount of the fluid.

DETAILED DESCRIPTION OF THE INVENTIVE CONCEPT

Technical Problem

The inventive concept provides a thin film bio valve device and an apparatus for controlling the same. The thin film bio valve device only uses a permanent magnet that generates a magnetic force to open or close a channel hole without generation of heat. In the thin film bio valve device, a magnetic valve that is moved due to a magnetic force formed between a fixed top permanent magnet disposed above the channel hole or an intermediate substrate formed of a ferromagnetic material and a movable permanent magnet disposed under the body is disposed to open or close the channel hole.

Technical Solution

According to an aspect of the inventive concept, there is provided a thin film bio valve device in which a channel and a channel hole are formed between neighboring chambers in a body, a top permanent magnet is fixed and disposed above the channel hole, and a movable permanent magnet is disposed under the body and at the same time a magnetic valve is disposed with respect to the channel hole, wherein the channel hole is closed due to an attractive force between the top permanent magnet and the magnetic valve, and then the magnetic valve is moved in a clockwise or anticlockwise according to an attractive force between the magnetic valve and the movable permanent magnet and a rotary direction of the body, thereby opening or closing the channel hole.

According to another aspect of the inventive concept, there is provided a thin film bio valve device in which a channel and a channel hole are formed between neighboring chambers in a body, a top permanent magnet is fixed and disposed above the channel hole, and a movable permanent magnet is disposed under the body and at the same time a magnetic valve is disposed with respect to the channel hole, wherein the channel hole is closed due to an attractive force between the top permanent magnet and the magnetic valve, and then the movable permanent magnet is space-addressed to generate an attractive force between the magnetic valve and the movable permanent magnet and thus, the magnetic valve is reversibly moved in a radial direction to open or close the channel hole.

According to another aspect of the inventive concept, there is provided a thin film bio valve device in which a channel and a channel hole are formed between neighboring chambers in a body, an intermediate substrate of the body is formed of a ferromagnetic material, and a movable permanent magnet is disposed under the body and at the same time a magnetic valve is disposed with respect to the channel hole, wherein the channel hole is closed due to an attractive force between the intermediate substrate and the magnet valve, and then, the movable permanent magnet is space-addressed toward a center of the channel hole to generate an attractive force between the magnetic valve and the movable permanent magnet, thereby opening the channel hole.

According to another aspect of the inventive concept, there is provided a thin film bio valve device in which a channel and a channel hole are formed between neighboring chambers in a body, an intermediate substrate of the body is formed of a ferromagnetic material, and a movable permanent magnet is disposed under the body and at the same time a magnetic valve is disposed with respect to the channel hole, wherein the channel hole is closed due to an attractive force between the intermediate substrate and the magnetic valve, and then the magnetic valve is moved in a clockwise or anticlockwise according to an attractive force between the magnetic valve and the movable permanent magnet and a rotary direction of the body, thereby opening or closing the channel hole.

According to another aspect of the inventive concept, there is provided a thin film bio valve device in which a channel and a channel hole are formed between neighboring chambers in a body, an intermediate substrate of the body is formed of a ferromagnetic material, and a movable permanent magnet is disposed under the body and at the same time a magnetic valve is disposed with respect to the channel hole, wherein the channel hole is closed due to an attractive force between the intermediate substrate and the magnetic valve, and then the movable permanent magnet is space-addressed to generate an attractive force between the magnetic valve and the movable permanent magnet and thus, the magnetic valve is reversibly moved in a radial direction to open or close the channel hole.

In other embodiments, the movable permanent magnet can be mounted on a slider, and the movable permanent magnet mounted on the slider can be replaced with a scan magnet mounted on an actuator.

1. According to another aspect of the inventive concept, there is provided a thin film bio valve device in which a channel and a channel hole are formed between neighboring chambers in a body, an intermediate substrate of the body is formed of a ferromagnetic material, a spiral magnetic pattern is formed on a top surface of the body, an actuator is disposed above the top surface of the body, and a movable permanent magnet is disposed under the body and at the same time a magnetic valve is disposed with respect to the channel hole, wherein the channel hole is closed due to an attractive force between the intermediate substrate and the magnetic valve and then, space-addressing in a radial direction is performed by the actuator and space-addressing in an azimuth direction is performed by the movable permanent magnet to generate an attractive force between the magnetic valve and the movable permanent magnet and thus, the magnetic valve is reversibly moved in an up and down direction, in a clockwise and/or counter-clockwise direction, or in a radial direction, thereby opening or closing the channel hole. That is, the space-addressing with respect to the magnetic valve comprises a radial space-addressing and an azimuth space-addressing.

The spiral magnet pattern may be a spiral-shaped ferromagnetic pattern or a magnetic pattern. The magnetic valve may be formed of a ferromagnetic material or a permanent magnet. The magnetic valve may be coated with metal or a rubber cushion material such as silicone rubber.

According to an embodiment of the inventive concept, the magnetic valve may be a thin film circular magnet, a thin film cylindrical magnet, a thin film tetragonal magnet, or a ball magnet. A rubber cushion material, such as a silicon rubber, may be coated on one surface of the thin film bio valve device.

According to an embodiment of the inventive concept, when the magnetic valve is a ball magnet, the channel hole may have a curvature of the ball magnet.

According to an embodiment of the inventive concept, instead of coating with the rubber cushion material, a thin film rubber may be inserted between the magnetic valve and the channel hole.

Hereinafter, as a contact portion with respect to the magnetic valve, formed when the channel hole is closed, a portion between an outer channel hole and an inner channel hole is referred to as a channel hole contact portion.

According to an embodiment of the inventive concept, the channel hole contact portion (that is, a contact portion with respect to the magnetic valve, formed between the outer channel hole and the inner channel hole) may have a circular groove. The coating with the rubber cushion material, the thin film rubber, and the circular groove may prevent leakage of a liquid when the magnetic valve is closed. The ferromagnetic material that forms the intermediate substrate may be a permanent magnet, or at least one material selected from the group consisting of iron, cobalt, chrome, nickel, and an alloy thereof. The thickness of the intermediate substrate may be in a range of 0.1 mm to 0.6 mm. The intermediate substrate formed of a ferromagnetic material may also be a plastic or aluminum disk coated with a magnetic material. An example of a method of coating the magnetic material on the aluminum disk comprises plating an aluminum substrate with nickel and forming a magnetized layer thereon by using a metal alloy of cobalt, nickel, or chrome. The intermediate substrate formed of a ferromagnetic material may also be formed by coating a magnetic material and an insulating material on an aluminum disk by using a pattern mask pattern. The coating with the insulating material may be performed by using a $SiO_2$ film. The coating with a magnetic material may provide a conductive pattern. The ferromagnetic material that forms the intermediate substrate may be formed of metal that is conductive, and the metal may be patterned using a mask to form an electric circuit pattern.

According to an embodiment of the inventive concept, the intermediate substrate of the thin film bio valve device may have an electric circuit pattern.

In the thin film bio valve device according to an embodiment of the inventive concept, the magnetic valve may be formed of a ferromagnetic material, a paramagnetic material, a semi-magnetic material, or a permanent magnet. The diameter of the magnetic valve may be a range of 1 mm to 5 mm, and the thickness of the magnetic valve may be in a range of 0.1 mm to 0.5 mm. The magnetic valve may have a thin film circular shape, a thin film rectangular shape, or a thin film cylindrical shape.

In the thin film bio valve device according to an embodiment of the inventive concept, the chamber may further include a vent for discharging air pressure generated by the flow of a fluid, and the vent may be disposed in a direction opposite to a direction in which the fluid flows, that is, a direction opposite to a direction in which a centrifugal force is applied.

In the thin film bio valve device according to an embodiment of the inventive concept, the body may further include a holding groove to prevent deviation of the magnetic valve.

According to an aspect of the inventive concept, there is provided a thin film bio valve device that includes: at least one chamber for containing a fluid required for biological and/or biochemical assay and/or chemical assay or in which these assays are performed; channels connecting the chambers; an assay site or biological reaction chamber in which a biological or biochemical reaction is performed with a sample; a channel hole that connects each of the channels and is disposed in the middle of the corresponding channel; a magnetic valve for opening or closing the channel hole; and a body in which the chambers, the channels, the assay site, the biological reaction chamber, the channel holes and the magnetic valves are integrated.

In the current specification, a biological or biochemical reaction refers to a specific binding reaction of two bio materials, a ligand-receptor reaction, an antigen-antibody reaction, an immunological reaction, a hybridization reaction, a biochemical reaction, or a three-dimensional change of a material caused by a reaction. A biochemical reaction refers to a reaction for assaying a material contained in a blood. Examples of the material contained in the blood include GOT, GPT, ALP, LDH, GGT, CPK, amylase, T-protein, albumin, glucose, T-cholesterol, triglycerides, T-bilirubin, D-bilirubin, BUN, creatinine, I. Phosphorus, calcium, and a uric acid.

A thin film bio valve device according to an embodiment of the inventive concept may be used in an assay device for diagnosing and/or detecting a small amount of bio material or chemical material in a fluid. Such an assay device may be a lap-on-a-chip to which a ELISA/CLISA assay method is applied, a lap-on-a-chip to which a rapid test is applied, or a lap-on-a-chip for a food poisoning virus examination, a residual antibiotics examination, a residual agricultural chemicals examination, a heavy metal in a polluted water examination, a transgenic foods examination, a food allergy examination, a pollutants examination, and a bacterium, such as a colon *bacillus* or a *salmonella*, examination, a meat examination, or an examination for identifying the place of origin.

According to an embodiment of the inventive concept, the bacterium examination may be a colon *bacillus* examination, a *pseudomonas aeroginosa* examination, a *staphylococcus* examination, a *vibrio* examination, or a *salmonella* examination.

According to an embodiment of the inventive concept, the residual agricultural chemicals examination is performed to detect an organic phosphorous-based or carbamate-based insecticide contained in vegetables, greens, or fruits. The organic phosphorous-based or carbamate-based insecticide is the most common insecticide.

According to an embodiment of the inventive concept, the bio material may include at least one material selected from the group consisting of DNA, oligo nucleotide, RNA, PNA, ligands, receptors, an antigen, an antibody, a milk, urine, saliva, hairs, a crop and/or vegetable sample, a meat sample, a fish sample, a bird sample, polluted water, a livestock sample, food materials for cooking, a food sample, an oral cell, a tissue sample, saliva, semen, a protein, and a living body material. The food materials for cooking may include food materials for cooking pot-stews, food materials for cooking noodles, food materials for making kimchi, food materials for cooking soups, and stocks. For a urine specimen, the thin film valve device may be used to assay leukocyte, blood, protein, nitrite, pH, specific gravity, glucose, ketone, ascorbic acid, urobilinogen, or bilirubin. For a hair specimen, a historical record made by accumulating minerals, nutrient materials and poisoning materials in a body may be accurately evaluated, compared to a blood or urine assay. In addition, the assay site can be used to accurately identify whether inorganic materials are excessive or lack and the amount of a poisoning heavy metal, and these usages are well known. A body of the thin film bio valve device may be a circular plate disk having the thickness of 1 mm to 10 mm and the diameter of 120 mm, 80 mm, 60 mm or 32 mm.

In the thin film valve device according to an embodiment of the inventive concept, the body of the thin film bio valve device may be formed by stacking and/or binding two or three substrates by using a thin film adhesive tape.

According to an embodiment of the inventive concept, the thickness of each of the substrates may be in a range of 0.1 mm to 0.6 mm.

In the thin film bio valve device according to an embodiment of the inventive concept, the body may be formed by stacking and/or binding a top substrate, an intermediate substrate, and a bottom substrate. The body may have a channel, a channel hole and/or a chamber. Specifically, in the top substrate, a chamber and a top channel extending to the channel hole are engraved to a predetermined depth; in the intermediate substrate, the channel hole is formed; and in the bottom substrate, another chamber and a bottom channel extending to the channel hole are engraved to a predetermined depth.

In the thin film bio valve device according to an embodiment of the inventive concept, the top and bottom channels may be thin film channels instead of engraved channels. The thin film channels may be formed by using a thin film adhesive tape without engraving.

In the thin film bio valve device according to an embodiment of the inventive concept, the thin film channels may be formed between substrates bound to each other by using a thin film adhesive tape in which a channel-shaped structure is formed. The substrates are bound to each other by using the thin film adhesive tape to form one body, and in this case, the thin film channels correspond to an opening of the thin film adhesive tape between the substrates. The thin film channels may have a very small thickness and thus, a capillary phenomenon may easily occur and a fluid may appropriately flow.

In the thin film bio valve device according to an embodiment of the inventive concept, the body may be formed of a material selected from the group consisting of silicon, aerogel, plastic, PMMA, glass, silicon, polypropylene, polyacrylate, polyvinylalcohol, polyethylene, polymethyl methacrylate (PMMA) cyclic olefin copolymer (COC), and polycarbonate.

In the thin film bio valve device according to an embodiment of the inventive concept, the body may be surface-coated with aluminum or an aluminum sheet to prevent evaporation of a liquid contained in chambers.

In the thin film bio valve device according to an embodiment of the inventive concept, the thin film adhesive tape may be formed in such a manner that double-sided tape is attached to a substrate and then a protective strip of the double-sided tape is removed so that one surface of the substrate is thin-film-coated with an adhesive, or that an adhesive is surface-coated on a substrate by using a dispenser, a spray, or a silk screen printing method so that one surface of the substrate is thin-film-coated with the adhesive. That is, according to an embodiment of the inventive concept, the thin film adhesive tape may be an adhesive or gluing agent in itself, and may be formed by thin-film-coating a substrate with the adhesive. The thin film adhesive tape may be any kind of an adhesive or gluing agent, such as single-sided tape or double-sided tape. Examples of the adhesive include a hot melt tape, silicon, rubbers, modified silicons, acrylics, ployamides, polyolefins, teflons, polyester, epoxy, ultraviolet (UV) curable adhesives, UV adhesives, a thermoplastic resin tape, gel, and wax.

According to an embodiment of the inventive concept, the adhesive may be a hot melt tape, a thermosetting tape, or a thermoplastic tape.

In the thin film bio valve device according to an embodiment of the inventive concept, a plurality of substrates coated with the adhesive may be brought into contact with each other to form one body.

In the thin film bio valve device according to an embodiment of the inventive concept, the thin film adhesive tape may be an aluminum thin film adhesive tape formed by coating facing surfaces of an aluminum sheet with an adhesive. In this case, the aluminum thin film adhesive tape may bind a plurality of substrates to form one body and also prevent evaporation of a liquid contained in chambers.

In the thin film bio valve device according to an embodiment of the inventive concept, the aluminum sheet of the aluminum thin film adhesive tape may provide a hydrophilic channel. That is, when a portion of the aluminum sheet for providing a hydrophilic channel is coated with an adhesive, a mask is used to prevent the portion of the aluminum sheet from being coated with the adhesive. As a result, when the substrates are bound by using the aluminum thin film adhesive tape, a hydrophilic channel may be formed in the body. That is, in the aluminum sheet, the portion coated with the adhesive is hydrophobic and the portion that is not coated with the adhesive is hydrophilic.

In the thin film bio valve device according to an embodiment of the inventive concept, the aluminum thin film adhesive tape may provide an electric circuit pattern, and electric circuits may be integrated in the body of the thin film valve device. That is, the body can be engraved to accommodate a semiconductor chip therein, and the semiconductor chip is combined with the electric circuit pattern to integrate various electric circuits in the thin film bio valve device. The aluminum thin film adhesive tape may provide electric circuit patterns to drive various electric components and/or semiconductor chips located in the body.

In the thin film bio valve device according to an embodiment of the inventive concept, the electric circuit pattern may be an interdigitated array electrode pattern for reading an assay site, a resistance pattern, or an electronic induced coil pattern.

In the thin film bio valve device according to an embodiment of the inventive concept, the interdigitated array electrode pattern may be an impedance measurement device for reading the assay site or an electrochemical detection device.

In the thin film bio valve device according to an embodiment of the inventive concept, the semiconductor chip may be a wireless RF IC. The wireless RF IC may generate a control signal for an impedance measurement device or an electrochemical detection device, and store results in a memory contained in the wireless RF IC or wirelessly transmit the results to an external device. In the aluminum thin film adhesive tape, a portion that is to be attached to a substrate may be coated with an adhesive, and a portion corresponding to the interdigitated array pattern may not be coated with the adhesive.

According to another aspect of the inventive concept, there is provided an apparatus for controlling a thin film bio valve device, the apparatus including: a spindle motor for rotating the thin film bio valve device; a slider on which a movable permanent magnet is mounted, wherein the movable permanent magnet is space-addressed by the slider; a slide motor for driving the slider; and a central control device for controlling the movement of the slider, space-addressing of the slider with respect to a channel hole to be opened or closed, and rotation of the thin film bio valve device, wherein the channel hole of the thin film bio valve device is opened or closed due to a magnetic force generated by a magnetic valve and the movable permanent magnet.

In the apparatus for controlling a thin film bio valve device according to an embodiment of the inventive concept, the space-addressing with respect to the channel hole to be opened or closed may include a space-addressing in a radial direction and a space-addressing in an azimuth direction. The space-addressing in the radial direction may be performed by the slider motor that may reversibly move the slider in the radial direction. According to a rotary direction of the slider motor, the slider is moved in the radial direction, that is, moved in a direction from the center of a body of the thin film bio valve device to the outside or in a direction from the outside to the center of the body.

In the apparatus for controlling a thin film bio valve device according to an embodiment of the inventive concept, the space-addressing in the azimuth direction is performed after the space-addressing in the radial direction is completed while the slider is stopped. The space-addressing in the azimuth direction slider may be performed by slowly turning the spindle motor, or by repeatedly performing a cycle of short-rotating and stopping the spindle motor. When the movable permanent magnet mounted on the slider is matched with a magnetic valve disposed at a corresponding radius by the slow-rotation and short-rotations of the spindle motor, a strong attractive force between the movable permanent magnet and the magnetic valve is generated and thus, the body of the thin film bio valve device is not rotated any more by the slow-rotation and short-rotations. In this way as described above, the space-addressing in the azimuth direction with respect to the channel hole to be opened or closed is performed.

In the apparatus for controlling a thin film bio valve device according to an embodiment of the inventive concept, the channel hole is closed due to an attractive force between a top permanent magnet and a magnetic valve or an attractive force between an intermediate substrate and the magnetic valve, and the movable permanent magnet generates an attractive force with respect to a magnetic valve to be opened or closed by space-addressing and thus, a channel hole is opened.

The apparatus for controlling a thin film bio valve according to the above embodiments may further include an azimuth search motor; and a gear connection member connecting the azimuth search motor to a rotary axis of the spindle motor, wherein the space-addressing in the azimuth direction is performed by rotating the spindle motor according to the rotation of the azimuth search motor. The azimuth search motor may be a stepping motor. When the space-addressing in the azimuth direction is performed, the azimuth search motor may be connected to the rotary axis of the spindle motor by the gear connection member, and when the space-addressing in the azimuth direction is not performed, the azimuth search motor may be separated from the rotary axis of the spindle motor.

In the apparatus for controlling a thin film bio valve device according to an embodiment of the inventive concept, the gear connection member may include a gear unit 1 that is fixed and connected to the rotary axis of the spindle motor, and a gear unit 2 that is fixed and connected to a rotary axis of the azimuth search motor, wherein the gear unit 1 is connected to or separated from the gear unit 2 according to a rotary direction of the azimuth search motor. The gear unit 2 may further include a worm gear connected to the rotary axis of the azimuth search motor and a cam. The cam may be a plane CAM or a three-dimensional cam, which are well known. The plane cam illustrates an outline or groove in a plane curve. The three-dimensional cam illustrates an outline or groove in a space curve.

In the apparatus for controlling a thin film bio valve device according to an embodiment of the inventive concept, the movable permanent magnet is space-addressed with respect to a magnetic valve to be opened or closed and then, the slider is moved forward or backward in the radial direction, thereby reversibly opening or closing the channel hole.

In the apparatus for controlling a thin film bio valve device according to an embodiment of the inventive concept, after the space-addressing is completed, a fluid flows due to a pumping force generated according to the forward and/or backward movement in the radial direction of the magnetic valve, wherein the forward and/or backward movement in the radial direction occurs when the movable permanent magnet rapidly approaches or moves away from the center of a corresponding channel hole.

In the apparatus for controlling a thin film bio valve device according to an embodiment of the inventive concept, after the movable permanent magnet is space-addressed in the radial direction with respect to the magnetic valve, the thin film bio valve device is reversibly rotated in a clockwise direction and/or counter-clockwise direction to reversibly open or close the channel hole.

An apparatus for controlling a thin film bio valve device according to an embodiment of the inventive concept uses a pulse valve. The pulse valve instantly allows a fluid to flow through a channel hole due to a centrifugal force applied to the fluid when the body rotates whenever a movable permanent magnet mounted on a slider is matched with a magnetic valve. When the thin film bio valve device rotates, whenever the movable permanent magnet mounted on the slider is matched with a corresponding magnetic valve, an attractive force between the magnetic valve closing the channel hole and the movable permanent magnet is generated and thus the channel hole is opened. When the movable permanent magnet mounted on the slider is not matched with a corresponding magnetic valve, the channel hole may be closed due to an attractive force between an intermediate substrate and the magnetic valve and an attractive force between a top permanent magnet and the magnetic valve. In this case, the opening time period of the channel hole may be a function of a rotary speed of the thin film bio valve device.

In the apparatus for controlling a thin film bio valve device according to an embodiment of the inventive concept, after the space-addressing is completed, a fluid flows due to upward and downward movement of a magnetic valve occurring when a movable permanent magnet rapidly approaches and/or moves away from the center of a corresponding channel hole and a pumping force applied to the fluid according to the rapid approach and/or moving away. For the upward and downward movement of the magnetic valve, the magnetic valve moves downward due to an attractive force between the magnetic valve and the movable permanent magnet generated when the movable permanent magnet rapidly approaches the center of the channel hole, and the magnetic valve moves upward due to an attractive force between the magnetic valve and a top permanent magnet and an attractive force between an intermediate substrate and the magnetic valve generated when the movable permanent magnet moves away from the center of the channel hole. Hereinafter, a fluid movement caused by the pumping force of the magnetic valve will be referred to as a "pumping fluid movement."

The "pulse valve" operates according to rotation of the body after the space-addressing in the radial direction is completed. The pulse valve may be used when a fluid having high viscosity is moved to a neighboring chamber due to a centrifugal force during rotation. A fluid having high viscosity, such as serum, may not move well even when the channel hole is opened. In this case, when the channel hole is opened during rotation, the fluid can be easily moved to the neighboring chamber due to a centrifugal force affecting the fluid.

According to another aspect of the inventive concept, there is provided an apparatus for controlling a thin film bio valve device, the apparatus including: a spindle motor for rotating the thin film bio valve device; a slider on which a movable permanent magnet is mounted, which is used to perform space-addressing in a radial direction; a slide motor for driving the slider; an actuator on which a scan magnet is mounted, which is used to perform space-addressing in an azimuth direction; a voice coil or stepping motor for driving the actuator; and a central control device for turning the actuator, moving the slider, and controlling rotation of the thin film bio valve device, wherein a channel hole of the thin film bio valve device is opened or closed due to a magnetic force generated between a magnetic valve and the movable permanent magnet. The space-addressing in the radial direction may be performed by moving the slider to a radius of a corresponding magnetic valve after the space-addressing in the azimuth direction is completed by the actuator.

In the apparatus for controlling a thin film bio valve device according to an embodiment of the inventive concept, the space-addressing in the azimuth direction may be performed in such a manner that the actuator is turned to a coordinate of a spiral magnet pattern corresponding to an azimuth to be addressed, and then the spindle motor is slowly turned or a cycle of short-rotating and stopping the spindle motor is repeatedly performed. When the scan magnet mounted on a front end of the actuator is matched with the spiral magnet pattern by the slow-rotation or short-rotations of the spindle motor, a strong attractive force between the scan magnet and the spiral magnet pattern is generated and thus a body of the thin film bio valve device is not rotated any more by the slow-rotation and/or short-rotations of the spindle motor. Accordingly, as described above, the space-addressing in the azimuth direction can be performed with respect to a channel hole to be opened or closed.

In the apparatus for controlling a thin film bio valve device according to an embodiment of the inventive concept, the channel hole is closed due to an attractive force between the intermediate substrate and the magnetic valve, and the channel hole is opened due to an attractive force between the magnetic valve and the movable permanent magnet, wherein the attractive force between the magnetic valve and the movable permanent magnet is generated by the space-addressing in the azimuth direction of the scan magnet and by the space-addressing in the radial direction of the movable permanent magnet.

According to another aspect of the inventive concept, there is provided an apparatus for controlling a thin film bio valve device, the apparatus including: a spindle motor for rotating the thin film bio valve device; an actuator having a front end on which a scan magnet is mounted, which is used to space-address in an azimuth direction the scan magnet; a voice coil or stepping motor for driving the actuator; and a central control device for turning the actuator, and controlling rotation of the thin film bio valve device, wherein a channel hole of the thin film bio valve device is opened or closed due to a magnetic force formed between the magnetic valve and the scan magnet. The movable permanent magnet and the scan magnet may be a thin film circular magnet, a thin film cylindrical magnet or a thin film tetragonal magnet.

In the apparatus for controlling a thin film bio valve device according to an embodiment of the inventive concept, the channel hole is closed due to an attractive force between a top permanent magnet and the magnetic valve or an attractive force between an intermediate substrate and the magnetic valve, and the scan magnet is mounted on the actuator and generates an attractive force with respect to a magnetic valve to be opened or closed by space-addressing in the radial and azimuth directions with respect to the magnetic valve, thereby opening the channel hole.

In the apparatus for controlling a thin film bio valve device according to an embodiment of the inventive concept, the space-addressing in the azimuth direction is performed after the space-addressing in the radial direction is completed while the actuator is stopped. The space-addressing in the azimuth direction slider may be performed by slowly turning the spindle motor, or by repeatedly performing a cycle of short-rotating and stopping the spindle motor. When the scan magnet is matched with a magnetic valve disposed at a corresponding radius by the slow-rotation and short-rotations of the spindle motor, a strong attractive force between the scan magnet and the magnetic valve is generated and thus, a body of the thin film bio valve device is not rotated any more by the slow-rotation and short-rotations. In this way as described above, the space-addressing in the azimuth direction with respect to a channel hole to be opened or closed is performed.

In the apparatus for controlling a thin film bio valve device according to an embodiment of the inventive concept, the channel hole is closed due to an attractive force between a top permanent magnet and the magnetic valve or an attractive force between an intermediate substrate and the magnetic valve, and the scan magnet generates an attractive force with respect to a magnetic valve to be opened or closed by space-addressing in the radial and azimuth directions with respect to the magnetic valve, thereby opening the channel hole.

The apparatus for controlling a thin film bio valve according to above embodiments further includes: an azimuth search motor; and a gear connection member connecting the azimuth search motor and the rotary axis of the spindle motor, wherein the spindle motor is rotated according to rotation of the azimuth search motor to perform space-addressing in the azimuth direction. The azimuth search motor may be a stepping motor. When the space-addressing in the azimuth direction is performed, the azimuth search motor may be connected to the rotary axis of the spindle motor by the gear connection member, and when the space-addressing in the azimuth direction is not performed, the azimuth search motor may be separated from the rotary axis of the spindle motor by the gear connection member In the apparatus for controlling a thin film bio valve device according to an embodiment of the inventive concept, actuators may be disposed in parallel above and under the thin film bio valve device so that space-addressing is performed with respect to the same position of the thin film bio valve device. In this case, the channel hole is closed due to an attractive force between an intermediate substrate and the magnetic valve, and on the other hand the channel hole is opened due to a combined force of a repulsive force between a scan magnet mounted on the actuator disposed above the thin film bio valve device and an attractive force between a scan magnet mounted on the actuator disposed under the thin film bio valve device and the magnetic valve.

According to another aspect of the inventive concept, there is provided an apparatus for controlling a thin film bio valve device, the apparatus including: a spindle motor for rotating the thin film bio valve device; a first slider on which a movable permanent magnet for performing a space-addressing in a radial direction is mounted; a second slider on which a movable permanent magnet for performing a space-addressing in an azimuth direction is mounted; a central control device for controlling movement of the first slider, the movement of the second slider, and rotation of the thin film bio valve device, wherein a channel hole of the thin film bio valve device is opened or closed due to a magnetic force between a magnetic valve and the movable permanent magnets.

In the apparatus for controlling a thin film bio valve device according to an embodiment of the inventive concept, the space-addressing in the azimuth direction may be performed in such a manner that the second slider is moved to a coordinate of a spiral magnet pattern corresponding to an azimuth to be addressed, and then a spindle motor is slowly rotated or a cycle of short-rotating and/or stopping of the spindle motor is repeatedly performed. When the movable permanent magnet mounted on the second slider is matched with the spiral magnet pattern by the slow-rotation or short-rotations of the spindle motor, a strong attractive force between the movable permanent magnet and the spiral magnet pattern is generated and thus a body of the thin film bio valve device is not rotated any more by the slow-rotation and/or short-rotations of the spindle motor. Accordingly, as described above, the space-addressing in the azimuth direction can be performed with respect to a channel hole to be opened or closed.

In an embodiment of the inventive concept, the spiral magnet pattern may be patterned in a top portion of the thin film bio valve device, or patterned in an azimuth turn-table fixed to a rotary axis of the spindle motor.

In the apparatus for controlling a thin film bio valve device according to an embodiment of the inventive concept, the channel hole is closed due to an attractive force between a top permanent magnet and the magnetic valve and/or an attractive force between an intermediate substrate and the magnetic valve, and is opened due to an attractive force between the magnetic valve and the movable permanent magnets generated by the space-addressing in the azimuth direction performed by the second slider and the space-addressing in the radial direction performed by the first slider.

The apparatus for controlling a thin film bio valve device according to above embodiments may further include an optical detector. Whenever the optical detector passes by a reference hole formed in the thin film bio valve device while the body rotates, a reference trigger signal is transmitted to the central control device.

In an embodiment of the inventive concept, the reference hole may be set as a zero degree of an azimuth. Based on the zero degree of the azimuth, an azimuth offset of an azimuth turn-table with respect to the thin film bio valve device and/or an azimuth offset of an azimuth search motor with respect to the thin film bio valve device may be set.

Advantageous Effects

A thin film bio valve device and an apparatus for controlling the thin film bio valve according to embodiments of the inventive concept may be effectively used in a valve structure of a thin film device, such as a lap-on-a-chip, a protein chip, or a DNA chip, for diagnosing and/or detecting a small amount of material contained in a fluid.

DESCRIPTION OF THE DRAWINGS

FIGS. 4 and 5 are sectional views of a thin film bio valve device using a magnetic valve that moves in a clockwise and/or counter-clockwise direction and an intermediate substrate formed of a ferromagnetic material, in order to explain an operating state of the thin film bio valve device, according to another embodiment of the inventive concept;

FIG. 6 and FIG. 7 are sectional views of a thin film bio valve device using a magnetic valve that moves in a radial direction and an intermediate substrate formed of a ferromagnetic material, in order to explain an operating state of the thin film bio valve device, according to another embodiment of the inventive concept;

FIGS. 9 through 12 are sectional views of thin film bio valve devices similar to those illustrated in FIGS. 4 through 7, but in which a top permanent magnet and an intermediate substrate formed of a non-magnetic material are used instead of the intermediate substrate formed of the ferromagnetic material, according to embodiments of the inventive concept;

FIG. 14 is a sectional view for explaining a process in which a magnetic valve of the thin film bio valve of FIG. 13 is moved into a slide out space due to a centrifugal force, according to an embodiment of the inventive concept;

FIG. 19 and FIG. 20 illustrate a USB connection unit for providing connection with the USB interface member, according to embodiments of the inventive concept;

FIGS. 21 through 25 are diagrams of a thin film bio valve device and an apparatus for controlling the thin film bio valve, according to embodiments of the inventive concept;

BEST MODE

Hereinafter, the inventive concept will be described in detail with reference to the attached drawings.

Figure 1:
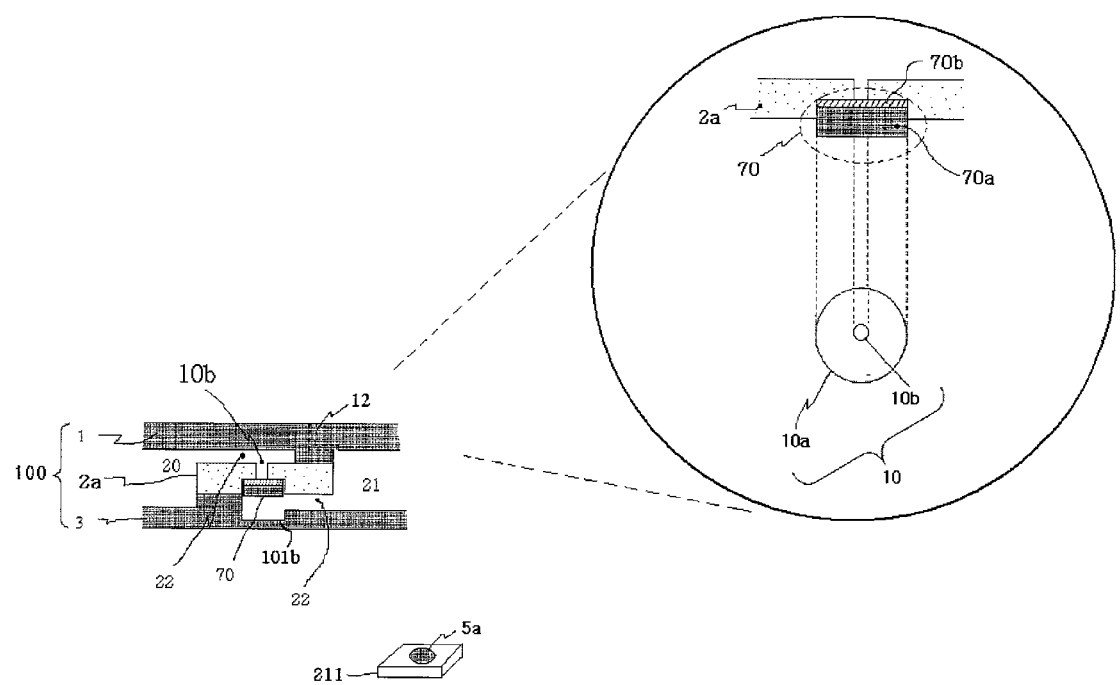
FIGS. 1 and 2 are sectional views of a thin film bio valve device using a magnetic valve that moves up and down and an intermediate substrate formed of a ferromagnetic material, in order to explain an operating state of the thin film bio valve device, according to an embodiment of the inventive concept.
Figure 2:
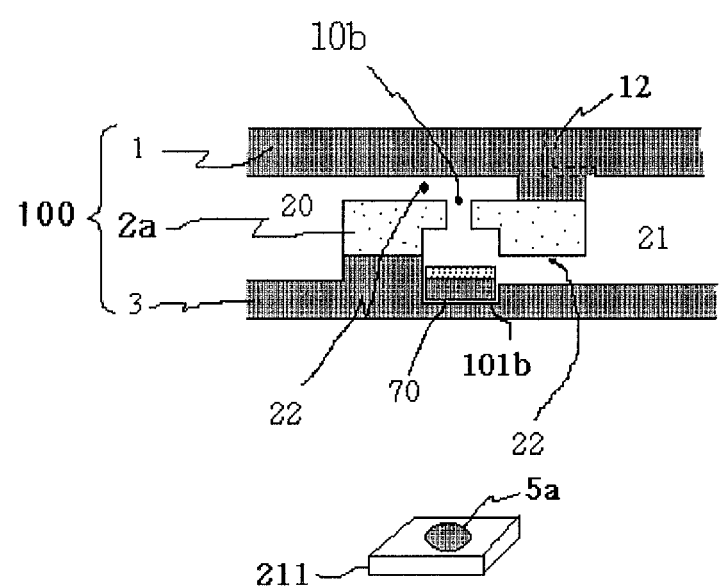

FIGS. 1 and 2 are sectional views of a thin film bio valve device using a magnetic valve 70 that moves up and down and an intermediate substrate 2a formed of a ferromagnetic material, to explain an operating state thereof, according to an embodiment of the inventive concept. Referring to FIGS. 1 and 2, the thin film bio valve device according to the present embodiment includes a body 100 including a top substrate 1, the intermediate substrate 2a, and a bottom substrate 3. In an injection molding process for forming the thin film bio valve device, a channel 22 through which a fluid flows along surfaces of the top substrate 1, intermediate substrate 2a, and bottom substrate 3; chambers 20 and 21 that are used to contain a buffer solution; and an inner channel hole 10b connecting the channel 22 are formed. The top substrate 1, the intermediate substrate 2a, and the bottom substrate 3 may be attached to each other to form the body 100.

FIG. 1 illustrates a case in which the inner channel hole 10b is closed by the magnetic valve 70 and thus the channel 22 is closed. FIG. 2 illustrates a case in which the inner channel hole 10b is opened and thus the channel 22 is connected. In the body 100, a vent 12 may be formed in the top substrate 1 so that the fluid smoothly flows through the channel 22 without air resistance. To close the channel hole 10b in order to close the channel 22 as illustrated in FIG. 1, a movable permanent magnet 5a mounted on a slider 211 is moved away from the center of the inner channel hole 10b and thus, the inner channel hole 10b is closed due to an attractive force between the intermediate substrate 2a and the magnetic valve 70. A channel hole contact portion 10 of the intermediate substrate 2a for accommodating the magnetic valve 70 may be formed by the inner channel hole 10b and an outer channel hole 10a. In some embodiments, the channel hole contact portion 10 may be formed by only a single channel hole.

An outer circumference of the channel hole contact portion 10 of the intermediate substrate 2a for accommodating the magnetic valve 70 is formed by the outer channel hole 10a, and an inner circumference of the channel hole contact portion 10 of the intermediate substrate 2a for accommodating the magnetic valve 70 is formed by the inner channel hole 10b. As a difference between a diameter of the outer channel hole 10a and a diameter of the inner channel hole 10b is increased, the channel hole contact portion 10 of the intermediate substrate 2a for accommodating the magnetic valve 70 is increased and leakage of the fluid is prevented. The channel hole contact portion 10 of the intermediate substrate 2a for accommodating the magnetic valve 70 is formed by the outer channel hole 10a and the inner channel hole 10b when the channel hole 10b is closed. In addition, the magnetic valve 70 may include a magnet 70a and a rubber cushion 70b coated on the magnet 70a. The rubber cushion 70b may be formed of a silicone rubber.

To open the inner channel hole 10b to connect the channel 22 as illustrated in FIG. 2, the slider 211 is space-addressed to match the movable permanent magnet 5a with the channel hole 10b and thus, the channel hole 10b is opened due to an attractive force between the movable permanent magnet 5a and the magnetic valve 70. That is, the attractive force between the movable permanent magnet 5a and the magnetic valve 70 is greater than that between the intermediate substrate 2a and the magnetic valve 70 and thus, the channel hole 10b is opened. This operation can be achieved by designing the movable permanent magnet 5a to have a strong magnetic force.

In addition, a holding groove 101b is formed in the bottom substrate 3 to accommodate the magnetic valve 70 in the bottom substrate 3 when the channel hole 10b is opened. The holding groove 101b prevents deviation of the magnetic valve 70 when the body 100 shakes. The diameter of the holding groove 101b may be 20% to 70% greater than that of the magnetic valve 70.

Figure 3:
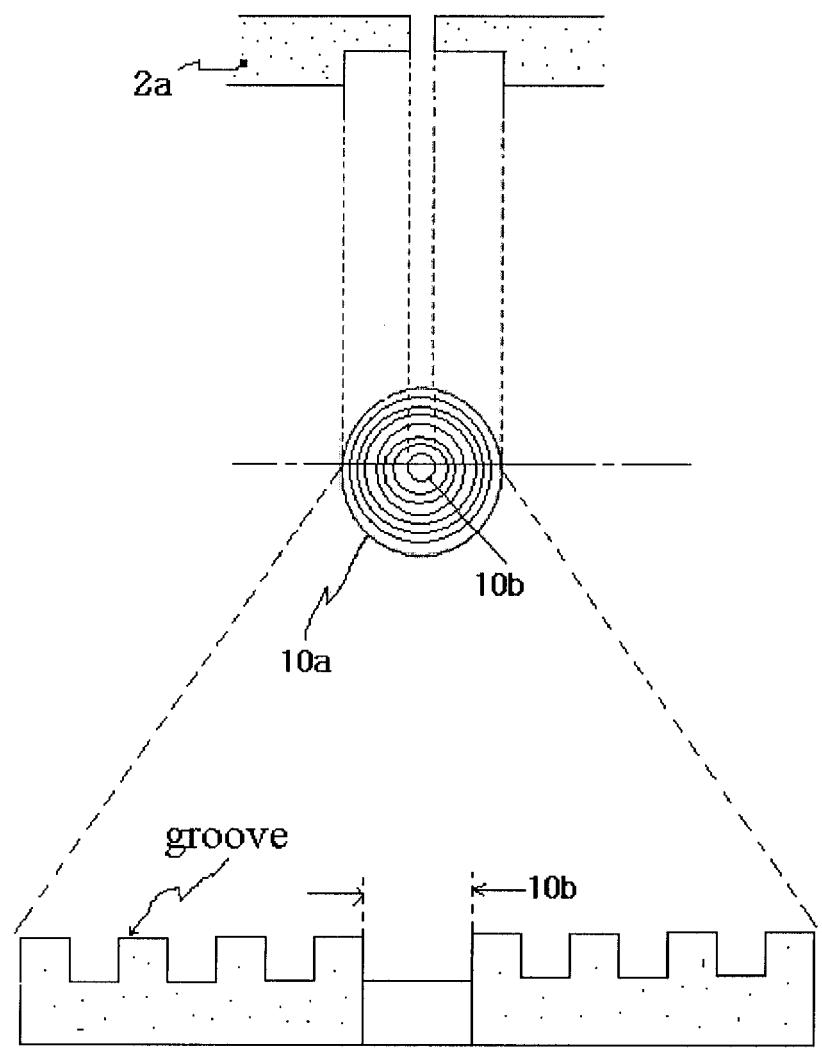
FIG. 3 illustrates a channel hole contact portion according to an embodiment of the inventive concept.

FIG. 3 illustrates the channel hole contact portion 10 in detail, that is, a contact portion for accommodating the magnetic valve 70, formed by the outer channel hole 10a and the inner channel hole 10b, according to an embodiment of the inventive concept.

FIGS. 4 and 5 are sectional views of a thin film bio valve device using a magnetic valve 70 that moves in a clockwise and/or counter-clockwise direction and an intermediate substrate 2a formed of a ferromagnetic material, in order to explain an operating state thereof, according to another embodiment of the inventive concept. Referring to FIGS. 4 and 5, the thin film bio valve device according to the present embodiment includes a body 100 including a top substrate 1, the intermediate substrate 2a, and a bottom substrate 3. In an injection molding process for forming the thin film bio valve device, a channel 22 through which a fluid flows along surfaces of the top substrate 1, intermediate substrate 2a, and bottom substrate 3, chambers 20 and 21 that are used to contain a buffer solution, and an inner channel hole 10b connecting the channel 22 are formed. The top substrate 1, the intermediate substrate 2a, and the bottom substrate 3 may be attached to each other to form the body 100.

FIG. 4 illustrates a case in which the inner channel hole 10b is closed by the magnetic valve 70 and thus the channel 22 is closed. FIG. 5 illustrates a case in which the inner channel hole 10b is opened and thus the channel 22 is connected. Referring to FIG. 4, to close the inner channel hole 10b in order to close the channel 22, a slider 211 is space-addressed to match a movable permanent magnet 5a with the inner channel hole 10b, and then, the body 100 is moved in an counter-clockwise direction and the magnetic valve 70 is thus moved in a clockwise direction along a circumference of the intermediate substrate 2a due to an attractive force between the magnetic valve 70 and the movable permanent magnet 5a, thereby closing the inner channel hole 10b. In this state, even when the slider 211 moves away from the center of the inner channel hole 10b, the magnetic valve 70 maintains the closed state of the inner channel hole 10b due to the attractive force with respect to the intermediate substrate 2a.

To open the inner channel hole 10b to connect the channel 22 as illustrated in FIG. 5, the slider 211 is space-addressed to match the movable permanent magnet 5a with the inner channel hole 10b, and then, the body 100 is moved in a clockwise direction and the magnetic valve 70 is thus moved in an counter-clockwise direction along the circumference of the intermediate substrate 2a due to the attractive force between the magnetic valve 70 and the movable permanent magnet 5a, thereby opening the inner channel hole 10b. In this state, even when the slider 211 moves away from the center of the inner channel hole 10b, the magnetic valve 70 maintains the open state of the channel hole 10b due to the attractive force with respect to the intermediate substrate 2a. That is, the inner channel hole 10b may be opened or closed according to the rotation direction of the body 100. A reference numeral 10c denotes an outer channel hole that forms an outer circumference of a contact portion of the intermediate substrate 2a for accommodating the magnetic valve 70 when the magnetic valve 70 is moved in the clockwise direction or counter-clockwise direction along the circumference of the intermediate substrate 2a. The reference numeral 10b denotes an inner channel hole that forms an inner circumference of the contact portion. The outer channel hole 10c may be designed to have a concentric circular shape so that when the body 100 rotates, deviation of the magnetic valve 70 caused by a centrifugal force is prevented. As the distance (Δr) between the outer channel hole 10c and the inner channel hole 10b is increased, the contact area between the magnetic valve 70 and the intermediate substrate 2a is increased. Thus, leakage of a fluid can be prevented.

Figure 6:
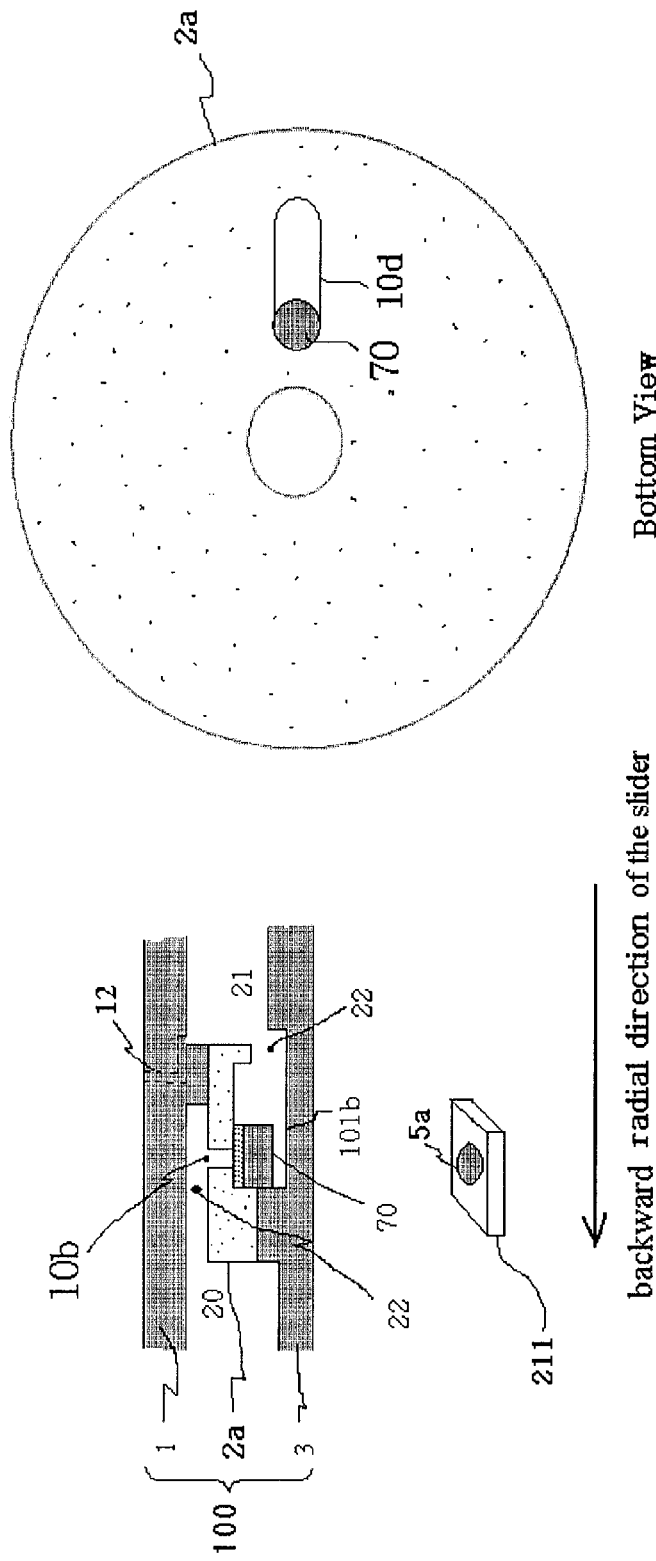

FIGS. 6 and 7 are sectional views of a thin film bio valve device using a magnetic valve 70 that moves in a radial direction and an intermediate substrate 2a formed of a ferromagnetic material, in order to explain an operating state thereof, according to another embodiment of the inventive concept. Referring to FIGS. 4 and 5, the thin film bio valve device according to the present embodiment includes a body 100 including a top substrate 1, the intermediate substrate 2a, and a bottom substrate 3. In an injection molding process for forming the thin film bio valve device, a channel 22 through which a fluid flows along surfaces of the top substrate 1, intermediate substrate 2a, and bottom substrate 3, chambers 20 and 21 that are used to contain a buffer solution, and an inner channel hole 10b connecting the channel 22 are formed. The top substrate 1, the intermediate substrate 2a, and the bottom substrate 3 may be attached to each other to form the body 100.

FIG. 6 illustrates a case in which the inner channel hole 10b is closed by the magnetic valve 70 and thus the channel 22 is closed. FIG. 7 illustrates a case in which the inner channel hole 10b is opened and thus the channel 22 is connected. To close the channel hole 10b as illustrated in FIG. 6, a movable permanent magnet 5a is moved in the vicinity of the center of the inner channel hole 10b by space-addressing of a slider 211 and then, the slider 100 is moved in a radial direction toward the center of the inner channel hole 10b. As a result, the magnetic valve 70 is moved toward the center of the inner channel hole 10b, that is, in a backward direction due to an attraction force between the magnetic valve 70 and the movable permanent magnet 5a and thus, the inner channel hole 10b is closed. In this state, even when the slider 211 is moved away from the inner channel hole 10b, the magnetic valve 70 maintains the closed state of the inner channel hole 10b due to the attractive force with respect to the intermediate substrate 2a. In this regard, the slider 211 may be moved toward the center of the body 100, or after the body 100 rotates by a small angle, the slider 211 may be moved away from the center of the inner channel hole 10b.

To open the inner channel hole 10b as illustrated in FIG. 7, the slider 211 is space-addressed to match the movable permanent magnet 5a with the inner channel hole 10b, and then, the slider 211 is moved away from the center of the inner channel hole 10b in a radial direction, that is, in a forward direction, and thus, the magnetic valve 70 is moved away from the center of the inner channel hole 10b due to the attractive force between the magnetic valve 70 and the movable permanent magnet 5a, thereby opening the inner channel hole 10b. In this state, even when the slider 211 is moved away from the inner channel hole 10b, the magnetic valve 70 maintains the open state of the inner channel hole 10b due to the attractive force with respect to the intermediate substrate 2a. In this regard, the slider 211 may be moved away from the body 100. That is, the inner channel hole 10b may be opened or closed when the slider 211 moving in the radial direction moves forward and/or backward.

A reference numeral 10d denotes an outer channel hole that forms an outer circumference of a contact portion of the intermediate substrate 2a for accommodating the magnetic valve 70 when the magnetic valve 70 is moved in the radial direction. The reference numeral 10b denotes an inner channel hole that forms an inner circumference of the contact portion. As the distance (Δr) between the outer channel hole 10d and the inner channel hole 10b is increased, the contact area between the magnetic valve 70 and the intermediate substrate 2a is increased. Thus, leakage of a fluid can be prevented.

Figure 8:
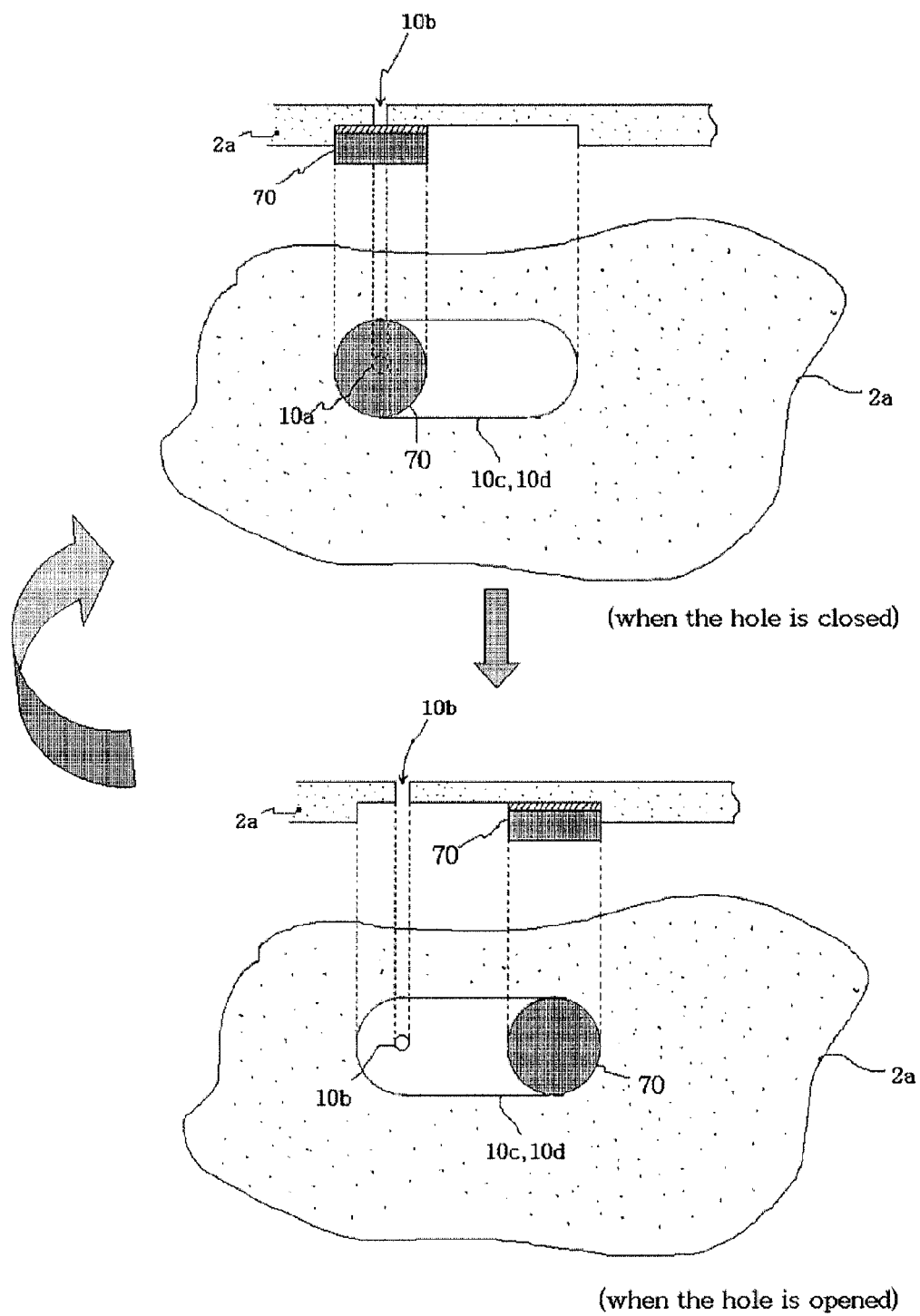
FIG. 8 is a detailed view of an outer channel hole, according to an embodiment of the inventive concept.

FIG. 8 is a detailed view of the outer channel holes 10c and 10d. When the magnetic valve 70 moves along the outer channel holes 10c and 10d, the inner channel hole 10b is opened or closed. In FIG. 8, the upper view illustrates a case in which the inner channel hole 10b is closed, and the lower view illustrates a case in which the inner channel hole 10b is opened.

FIGS. 9 through 12 are sectional views of thin film bio valve devices similar to those illustrated in FIGS. 4 through 7, but in which a top permanent magnet 4a and an intermediate substrate 2b formed of a non-magnetic material are used instead of the intermediate substrate 2a formed of the ferromagnetic material, according to embodiments of the inventive concept. The intermediate substrate 2b may be formed of the same material that is used to form a top substrate 1 or a bottom substrate 3.

Figure 9:
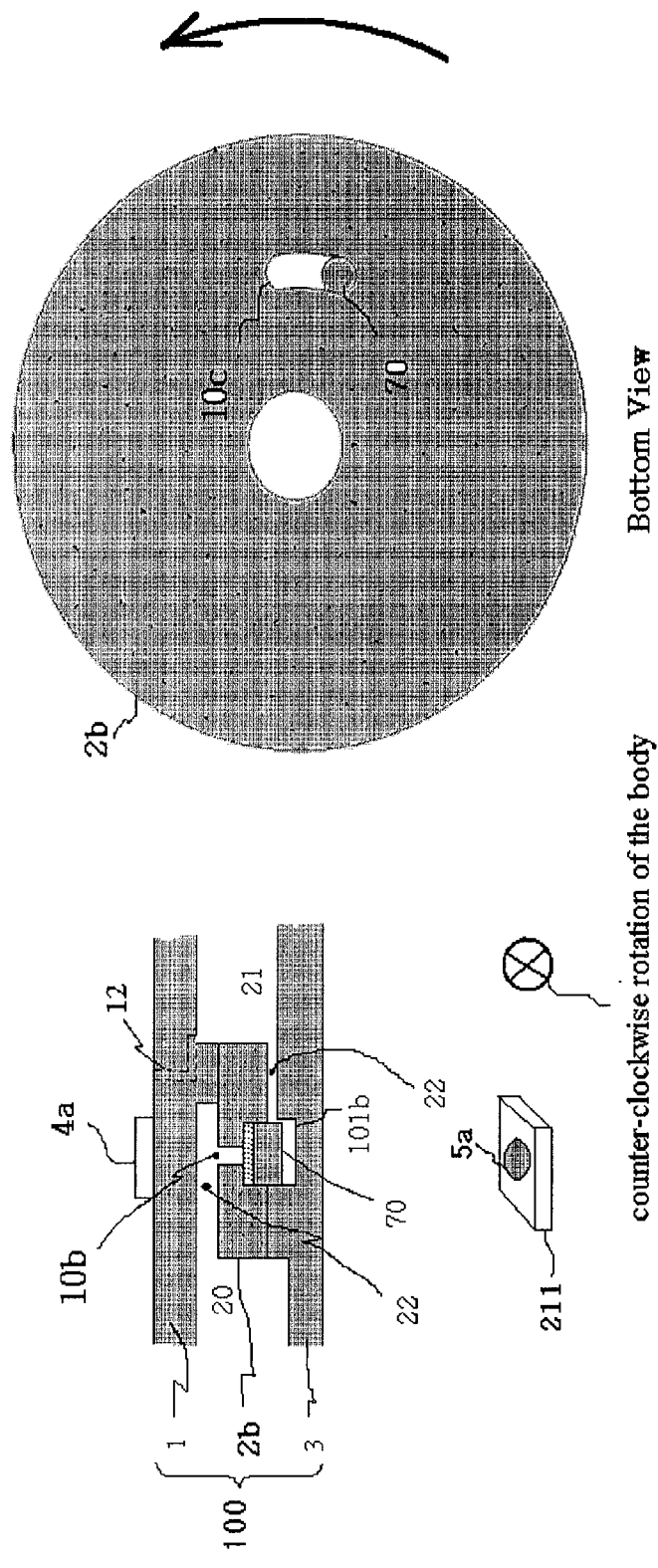
Figure 10:
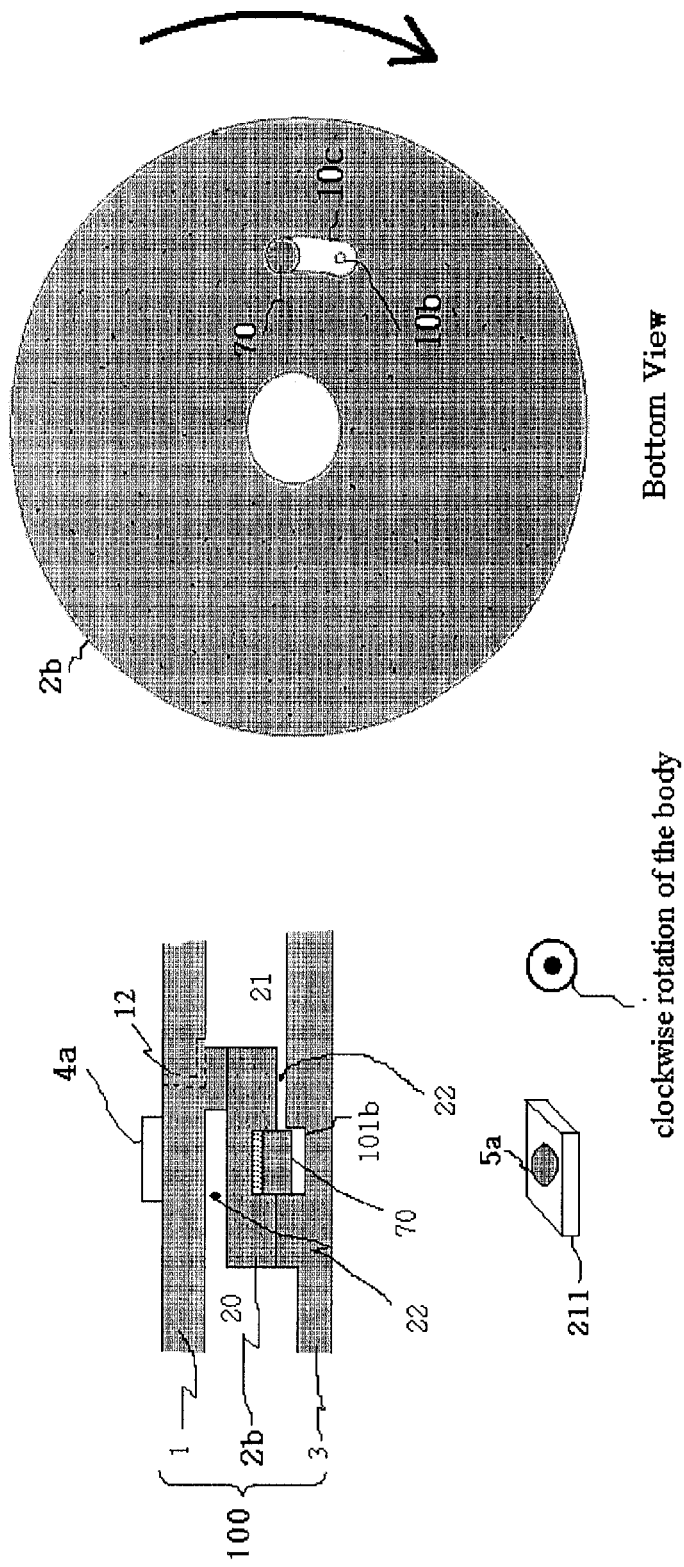
Figure 11:
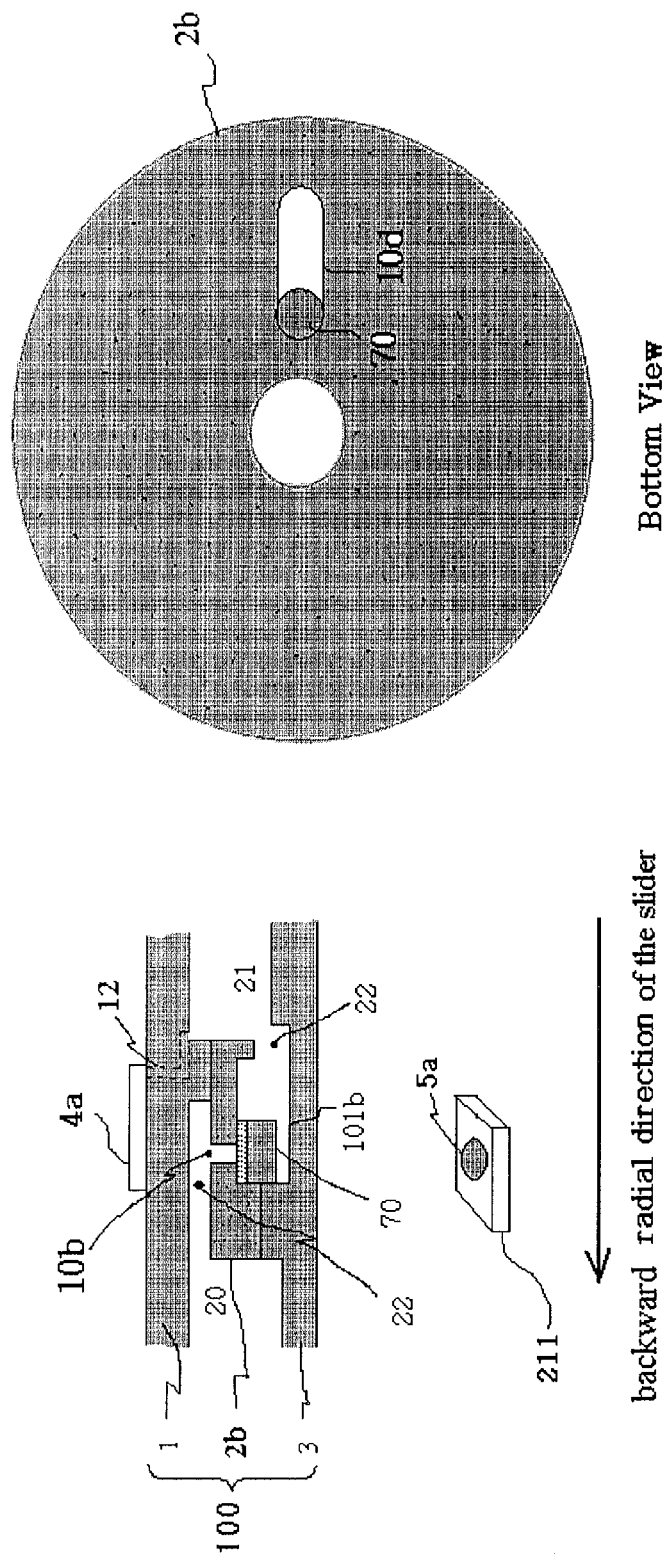

FIGS. 9 and 10 are sectional views of a thin film bio valve device using a magnetic valve 70 that moves in a clockwise and/or counter-clockwise direction and a top permanent magnet 4a, in order to explain an operating state thereof, according to another embodiment of the inventive concept. FIGS. 11 and 12 are sectional views of a thin film bio valve device using a magnetic valve 70 that moves in a radial direction and a top permanent magnet 4a, in order to explain an operating state thereof, according to another embodiment of the inventive concept. Due to an attraction force between the movable permanent magnet 5a and the magnetic valve 70, the magnetic valve 70 is moved in a clockwise or counter-clockwise direction or in a radial direction and thus an inner channel hole 10b is opened or closed. Then, due to an attractive force between the top permanent magnet 4a and the magnetic valve 70, the closing or opening state of the magnetic valve 70 can be maintained.

Figure 13:
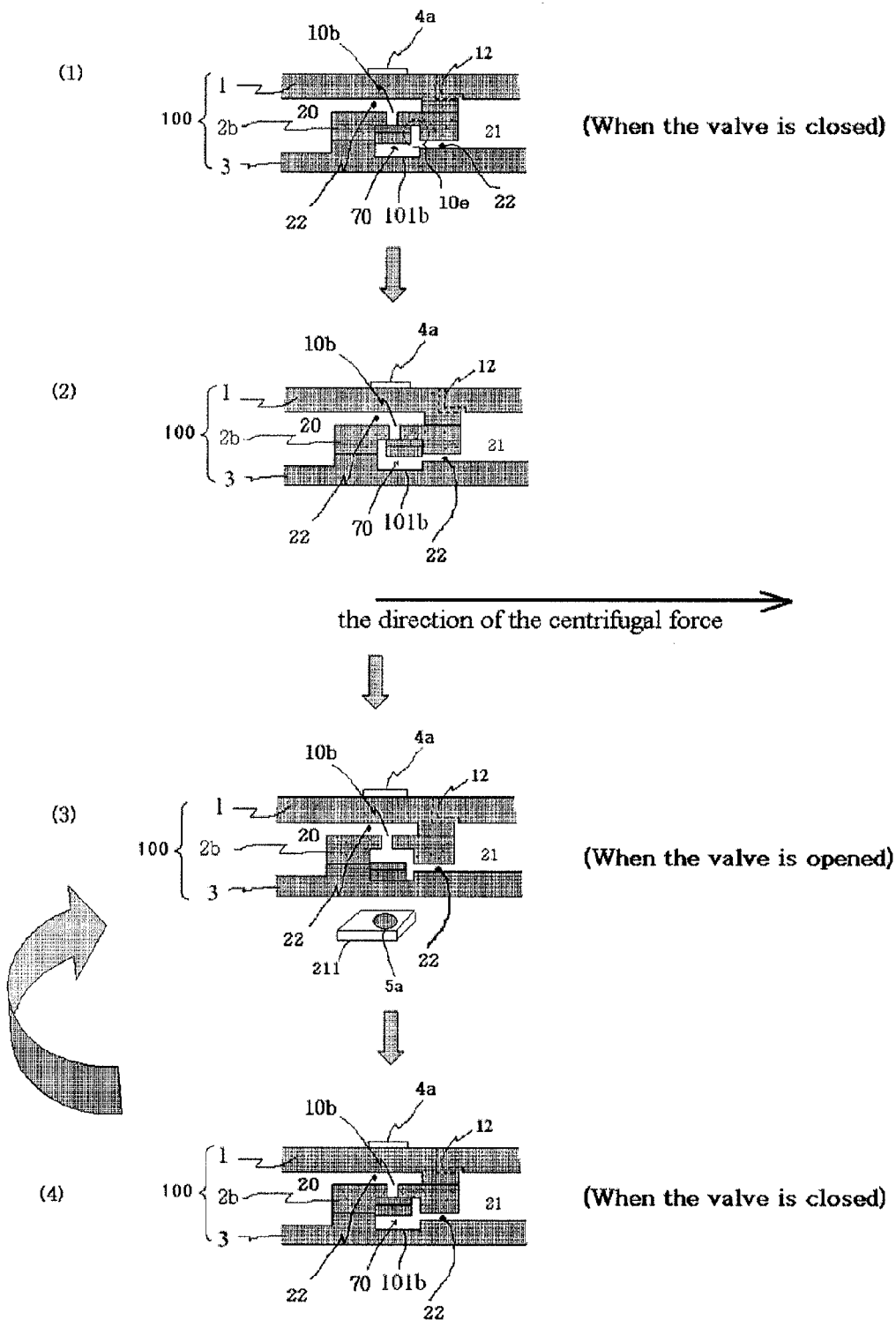
FIG. 13 is a sectional view of a thin film bio valve device according to another embodiment of the inventive concept.

FIGS. 13A through 13D are sectional views of a thin film bio valve device according to another embodiment of the inventive concept. Referring to FIGS. 13A and 13B, the thin film bio valve device according to the current embodiment has a reversible opening and closing function and includes a body 100. In the body 100, a channel 22 and a channel hole 10b are formed between neighboring chambers 20 and 21 and a magnetic valve 70 is disposed on the channel hole 10b. In this case, the channel hole 10b is closed due to an attractive force between a top permanent magnet 4a and the magnetic valve 70. To open the channel hole 10b, a centrifugal force is used to reduce an adhesion force between a rubber cushion (see 70b of FIG. 1) and a channel hole contact portion (see 10 of FIG. 1) and then, the channel hole 10b is opened by a permanent magnet 50a disposed below the body 100, thereby connecting the channel 22 between the neighboring chambers 20 and 21. Then, to close the channel hole 10b, the permanent magnet 5a is moved away from the center of the channel hole 10b. As a result, the channel hole 10b is closed by the magnetic valve 70 due to the attractive force between the top permanent magnet 4a and the magnetic valve 70.

FIG. 13A illustrates a case in which the channel hole 10b is closed by the magnetic valve 70 and thus, the channel 22 is closed. FIG. 13B illustrates a case in which the magnetic valve 70 slides out of the channel hole 10b due to a centrifugal force and thus, an adhesion force between the channel hole contact portion 10 and the rubber cushion 70b is reduced. When the channel hole 10b is opened for the first time after a long distribution period, the adhesion force between the rubber cushion 70b and the channel hole contact portion 10 is too strong and thus, the magnetic force of the movable permanent magnet 50a disposed under the body 100 is not enough to open the channel hole 10b. Accordingly, the adhesion force between the rubber cushion 70b and the channel hole contact portion 10 is needed to be reduced by moving the magnetic valve 70 away from the channel hole 10b into a slide-out space 10e in a radial movement. Once the magnetic valve 70 is moved, the magnetic valve 70 can be easily moved by using only the magnetic force of the permanent magnet 50a disposed under the body 100 and thus the channel hole 10b is opened. In FIG. 13B, even when the magnetic valve 70 is slid out of the channel hole 10b due to the centrifugal force, the channel hole 10b is still closed. FIG. 13C illustrates a case in which the magnetic valve 70 moves downward from the channel hole 10b due to the attractive force between the permanent magnet 5a and the magnetic valve 70 and thus, the channel hole 10b is opened. In this case, the neighboring chambers 20 and 21 are connected by the channel 22. FIG. 13D illustrates a case in which the magnetic valve 70 contacts the channel hole 10b due to the attractive force between the top permanent magnet 4a and the magnetic valve 70 and thus, the channel hole 10b is closed. That is, when the slider 211 is moved away from the center of the channel hole 10b, the magnetic valve 70 is brought into contact with the channel hole 10b due to the attractive force between the magnetic valve 70 and the top permanent magnet 4a. The rubber cushion 70b may be formed of a rubber-based material. For example, the rubber cushion 70b may be a silicon rubber film having a thickness of 0.1 to 0.5 mm and a diameter of 60% to 100% of a magnet (see 70a of FIG. 1) of the magnetic valve 70. The silicon rubber film may provide sealing and adhesion functions.

Referring to FIGS. 13A through D, since the thin film bio valve device according to the current embodiment includes the outer channel hole 10c illustrated in FIGS. 4, 5, 9, and 10, the magnetic valve 70 is moved in a clockwise and/or counterclockwise direction due to the attractive force between the magnetic valve 70 and the movable permanent magnet 5a and thus, the channel hole 10b is opened.

Like the thin film bio valve devices illustrated in FIGS. 4 to 7, the thin film bio valve device illustrated in FIGS. 13A through 13D may use an intermediate substrate 2a formed of a ferromagnetic material instead of the top permanent magnet 4a and the intermediate substrate 2b formed of the non-magnetic material.

FIG. 14 is a diagram for explaining a process in which the magnetic valve 70 is moved into the slide out space 10e due to the centrifugal force. The upper view of FIG. 14 illustrates a case in which the channel hole 10b is closed by the magnetic valve 70, and the lower view illustrates a case in which the magnetic valve 70 is moved into the slide out space 10e due to the centrifugal force and thus, an attractive force between the channel hole 10b and the rubber cushion 70b is reduced. The slide out space 10e is defined by intermediate substrates 2a and 2b and formed by extending an outer channel hole 10a in a centrifugal direction. The slide out space 10e provides a movement space for the magnetic valve 70 so that the magnetic valve 70 can slide out due to the centrifugal force. Referring to FIG. 14, although the magnetic valve 70 is moved into the slide out space 10e, the channel hole 10b is still closed.

An apparatus for controlling a thin film bio valve according to an embodiment of the inventive concept applies a centrifugal force that affects a fluid when the body rotates; and includes a "pulse valve" through which the fluid instantly flows through the channel hole 10b that is opened whenever the permanent magnet 5a disposed on the slider 211 is matched with the magnetic valve 70 when the body 100 rotates. When a thin film bio valve device rotates, whenever the permanent magnet 5a is matched with the magnetic valve 70, an attractive force between the magnetic valve 70 closing the channel hole 10b and the permanent magnet 5a is generated and thus, the channel hole 10b is opened. However, when the permanent magnet 5a is not matched with the magnetic valve 70, the channel hole 10b is closed due to the attractive force between the top permanent magnet 4a and the magnetic valve 70 or the attractive force between the intermediate substrate 2a and the magnetic valve 70. In this case, the opening time of the channel hole 10b may be a function of a rotation rate of the thin film bio valve device.

An apparatus for controlling a thin film bio valve according to another embodiment of the present invention applied a centrifugal force that affects a fluid when the body rotates; and includes a "pulse valve" in which the magnetic valve 70 is moved into the "slide out space 10e" formed in the outer channel hole 10a due to a sliding movement in a centrifugal direction caused by the centrifugal force and thus, the adhesion force between the rubber cushion 70b and the channel hole contact portion 10 is decreased and then the fluid gradually flows through the channel hole 10b that is opened whenever the permanent magnet 5a is matched with the magnetic valve 70.

Figure 15:
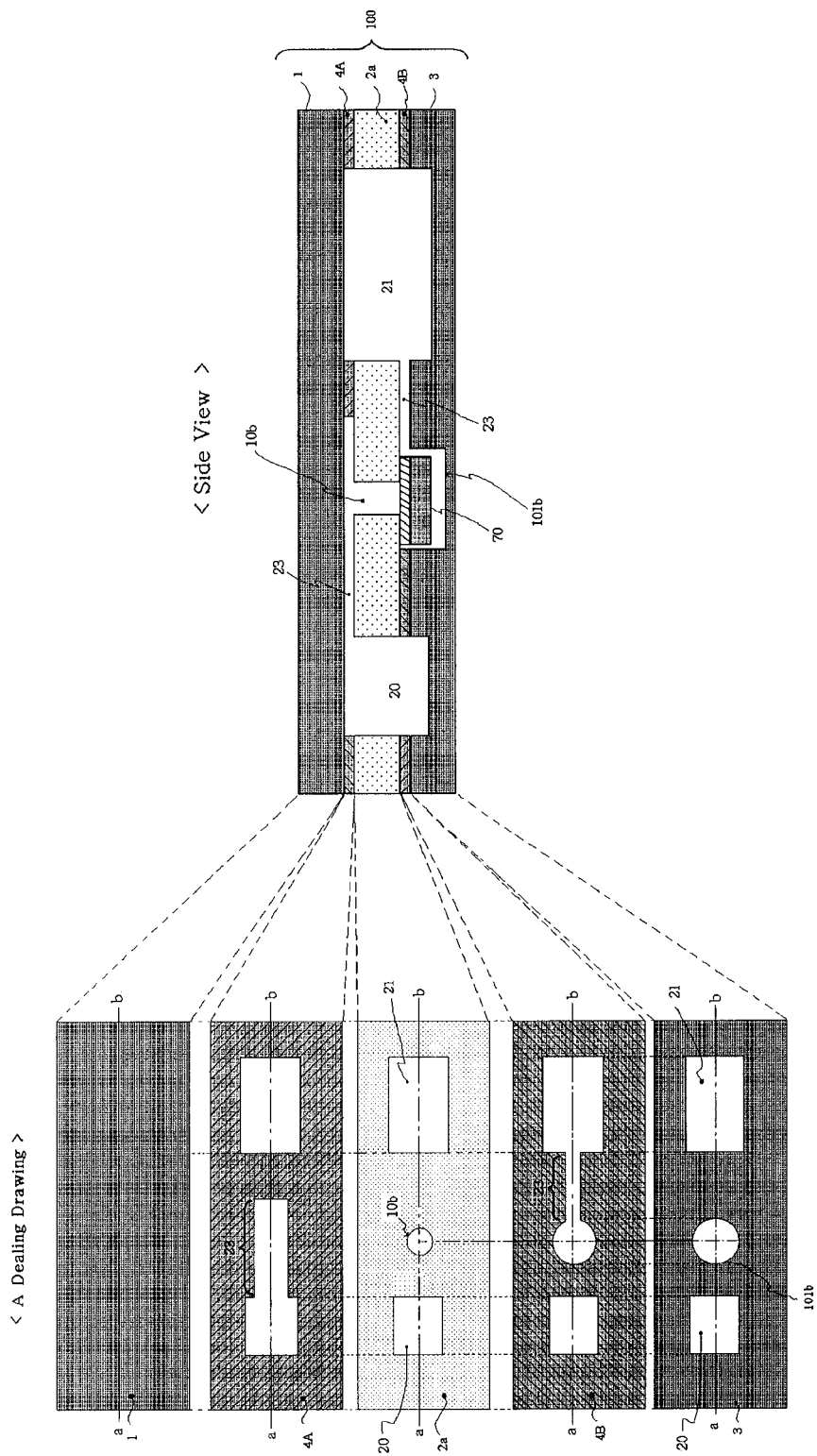
FIG. 15 is a sectional view of a thin film bio valve device similar to that illustrated in FIG. 1, wherein the channel of FIG. 1 is replaced with a thin film channel and an outer channel hole illustrated in FIG. 1 also functions as a holding groove of a bottom substrate so that a body of the thin film bio valve device is formed to have a small thickness, according to an embodiment of the inventive concept.

FIG. 15 illustrated an exploded view of a thin film bio valve device according to another embodiment of the inventive concept and a sectional view taken along a line a-b in the exploded view. In the current embodiment, the channel 22 illustrated in FIG. 1 is replaced with a thin film channel 23 and the outer channel hole 10a illustrated in FIG. 1 is replaced with a holding groove 101b of a bottom substrate 3, and thus, the thickness of a body 100 of the thin film bio valve device according to the current embodiment is reduced. Referring to FIG. 15, a channel hole 10b is closed by an attractive force between an intermediate substrate 2a formed of a ferromagnetic material and a magnetic valve 70. In the current embodiment, the holding groove 101b has, in addition to a holding function of its own, the function of the outer channel hole 10a illustrated in FIG. 1 and thus, the thickness of the body 100 may be further reduced. The thin film channel 23 may be formed by using thin film adhesive tapes 4A and 4B having a channel-shape opening while corresponding substrates are not engraved. That is, the thin film channel 23 may be formed by using the thin film adhesive tapes 4A and 4B having a channel-shape opening between top and bottom substrates 1 and 2 and thus, the thickness of the body 100 may be reduced. Top, intermediate, and bottom substrates 1, 2a, and 3 may be bonded to each other by the thin film adhesive tapes 4A and 4B, thereby forming the body 100. In this case, the thin film channel 23 may be defined by the channel-shape opening of the thin film adhesive tapes 4A and 4B between the top and bottom substrates 1 and 2. Since the thin film channel 23 may be formed to a very small thickness, a capillary phenomenon may easily occur and thus, the fluid may easily flow. The channel hole 10b may be located at the center of the pathway of the thin film channel 23 connecting neighboring chambers 20 and 21.

Figure 16:
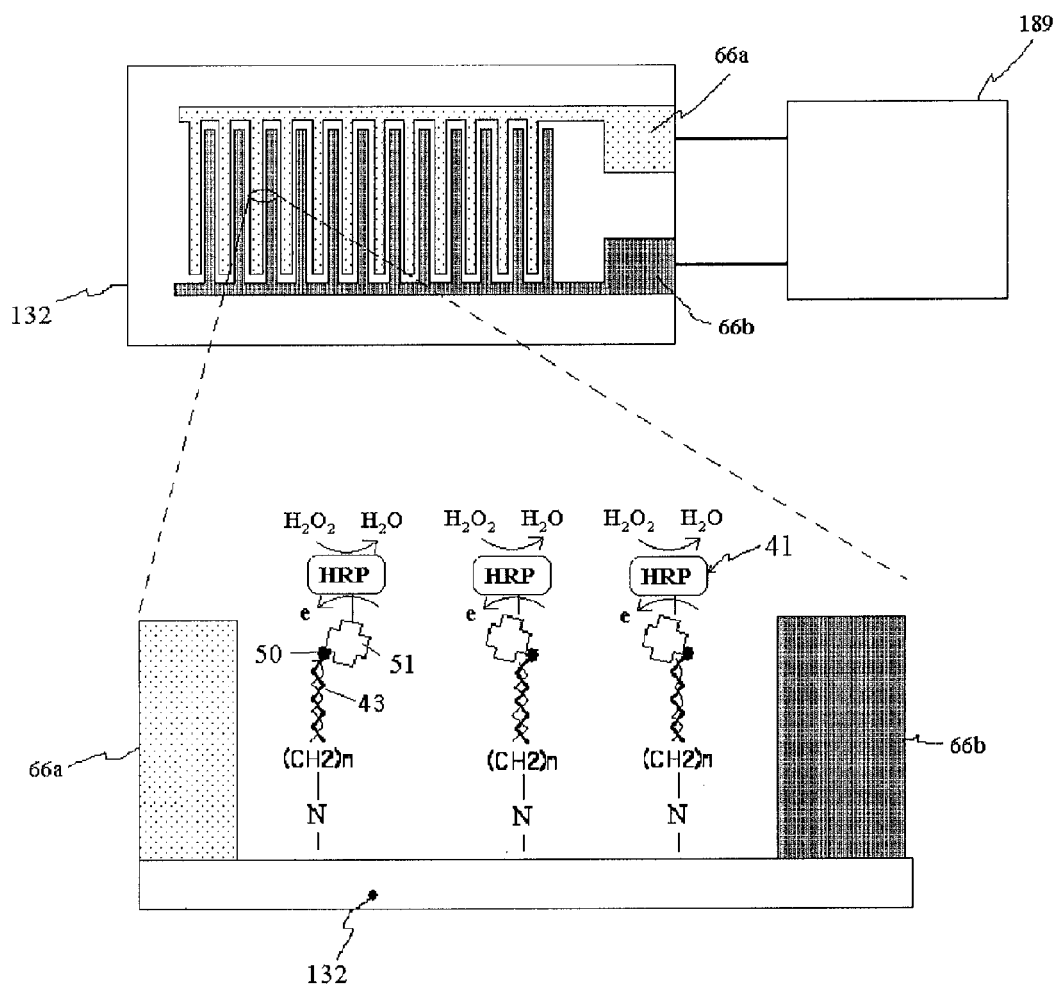
FIG. 16 is a diagram of an electrochemical detection device to which an interdigitated array electrode and a HorseRadish Peroxidase (HRP) are attached, wherein the electrochemical detection device uses a capture probe, according to an embodiment of the inventive concept.

FIG. 16 is a view of an electrochemical detection apparatus according to an embodiment of the inventive concept. Referring to FIG. 16, the electrochemical detection apparatus according to the present embodiment uses interdigitated array electrodes 66a and 66b disposed on a top substrate 1 or a bottom substrate 3 and a HorseRadish Peroxidase (HRP)-attached capture probe 43, in order to detect a specific binding reaction between bio materials in an assay site 132 disposed in the thin film bio valve device 100 illustrated in FIG. 15. The electrochemical detection can be achieved in such a manner that a control unit 189 measures a voltage and/or current generated by a redox reaction caused by HRP in the presence of a $H_2O_2$ solution. The voltage and/or current is applied to the interdigitated array electrodes 66a and 66b by electrons generated by the redox chain reaction. The electrochemical detection apparatus may have a higher degree of detection as a digit number of the interdigitated array electrodes 66a and 66b is increased.

Hereinafter, methods of detecting a specific binding reaction of bio materials according to various embodiments will be described in detail, using the electrochemical detection apparatus illustrated in FIG. 16.

(1) Hybridization Detection Method 1

The assay site 132 may be prepared in such a manner that a substrate is surface-treated with amine and a monolayer of non-reactive molecules, such as $(CH_2)_n$: alkane chain, is formed on the surface of the substrate in order to prevent a direct contact between the HorseRadish Peroxidase (HRP)-attached capture probe 43 labeled with a biotin 50 and a surface of the substrate and then, the HorseRadish Peroxidase (HRP)-attached capture probe 43 labeled with the biotin 50 is deposited on the surface of the substrate. Since capture probes that are not hybridized after a sample is loaded and thus maintained in a single strand are removed after a cleavage process performed by being brought into contact with nucleases and a washing process, only a double strand that is hybridized remains on the surface. Then, HRP 41 labeled with a streptavidin 51 is introduced and combined with the HorseRadish Peroxidase (HRP)-attached capture probe 43 labeled with the biotin 50 to form a streptavidin-biotin bond. Then, the control unit 189 measures a voltage and/or current applied to an interdigitated array, wherein the voltage and/or current is generated by a redox reaction caused by HRP in the presence of a $H_2O_2$ solution, thereby enabling electrochemical detection. This method provides a detection apparatus with a graded electrochemical signal with respect to capture probes that are not hybridized.

(2) Hybridization Detection Method 2

The assay site 132 may be prepared in such a manner that substrates 1 and 3 are surface-treated with amine and then, a capture probe that has a DNA sequence complementary to a base sequence to be assayed and is labeled with HRP is deposited on a surface of the substrates 1 and 3. Then, DNA extracted from a sample is loaded onto the assay site 132. Since capture probes that are not hybridized after the sample is loaded and thus maintained in a single strand are removed after a cleavage process performed by being brought into contact with nucleases and a washing process, only a double strand that is hybridized remains on the surface while HRP is maintained at an end of the double strand. After the washing process, the control unit 189 measures a voltage and/or current applied to an interdigitated array, wherein the voltage and/or current is generated by a redox reaction caused by HRP in the presence of a $H_2O_2$ solution, thereby enabling electrochemical detection. This method provides a detection apparatus with a graded electrochemical signal with respect to capture probes that are not hybridized.

(3) Hybridization Detection Method 3

The assay site 132 may be prepared in such a manner that substrates 1 and 3 are surface-treated with amine or a thiol group and then, a restriction probe is ligated to an end of a capture probe that has a DNA sequence complementary to a base sequence to be assayed and is labeled with HRP and then immobilized to a surface of the substrates 1 and 3. The restriction probe may have a sequence that is not hybridized with a target DNA. A DNA extracted from a sample is loaded onto the assay site 132. Capture probes that are maintained in a double strand due to hybridization after the sample is loaded are subjected to a cleavage process performed by contact with DNA extension and/or a contact with a restriction enzyme and then, removed from the surface of the substrates 1 and 3. Only a DNA that has a single strand and is not hybridized remains on the substrates 1 and 3 while HRP is ligated to an end of the DNA. Then, the control unit 189 measures a voltage and/or current applied to an interdigitated array, wherein the voltage and/or current is generated by a redox reaction caused by HRP in the presence of a $H_2O_2$ solution, thereby enabling electrochemical detection. This method provides a detection apparatus with a graded electrochemical signal with respect to capture probes that are hybridized. The base sequence of the capture probe is specifically determined according to an assay species to be diagnosed and/or assayed. After the capture probe is brought into contact with a sample having a target nucleic acid having the base sequence complementary to the capture probe, the capture probe is hybridized with the target nucleic acid to form a double strand. However, the restriction probe at the end of the capture probe is not double-stranded and remains in a single strand. To form the restriction probe that is not hybridized into a double strand, four types of dNTP mixed solution and a DNA polymerization solution including a DNA polymerase, which are required for DNA extension, are used. The restriction probe is double-strand by performing DNA extension using the target nucleic acid hybridized to the capture probe as a primer. When the capture probe is double-stranded by hybridization of the target nucleic acid to the capture probe; and double-stranding of the restriction probe due to the DNA extension, the double-stranded restriction probe may be cleaved by a restriction enzyme. Accordingly, after being cleaved by the restriction enzyme, the completed double strand is separated from the surface of the substrates 1 and 3 by using a washing process. On the other hand, when the capture probe is brought into contact with a sample that does not include the base sequence complementary to the capture probe, a double strand is not formed. Therefore, even after the addition of the restriction enzyme and the washing process, the capture probe continues to be attached to the substrates 1 and 3.

(4) Hybridization Detection Method 4

The assay site 132 may be prepared in such a manner that substrates 1 and 3 are surface-treated with amine and then, a capture probe having a DNA sequence complementary to a base sequence to be assayed is deposited on a surface of the substrates 1 and 3. Then, DNA extracted from a sample is labeled with HRP and the HRP-labeled DNA is loaded onto the assay site 132. Then, a washing process is performed and thus, only double-stranded DNA that is hybridized remains on the substrates 1 and 3 while HRP is ligated to the end of the double-stranded DNA. After the washing process is performed, the control unit 189 measures a voltage and/or current applied to an interdigitated array, wherein the voltage and/or current is generated by a redox reaction caused by HRP in the presence of a $H_2O_2$ solution, thereby enabling electrochemical detection. This method provides a detection apparatus with a graded electrochemical signal with respect to capture probes that are not hybridized.

(5) Antigen-Antibody Reaction Detection Method

The assay site 132 may be prepared in such a manner that a substrate is surface-treated with amine, and then an antibody that is specifically combined with an antigen to be assayed is deposited on a surface of the substrate. An HRP-labeled antigen as a sample is loaded onto the assay site 132. After a washing process is performed, only antigen that is specifically combined with the antibody remains on the substrate. After the washing process is performed, the control unit 189 measures a voltage and/or current applied to an interdigitated array, wherein the voltage and/or current is generated by a redox reaction caused by HRP in the presence of a $H_2O_2$ solution, thereby enabling electrochemical detection. This method provides a detection apparatus with a graded electrochemical signal with respect to an antibody that does not cause an antigen-antibody reaction.

In addition, a thin film bio valve device including the assay site 132 illustrated in FIG. 16 may be used as an impedance measurement device that is embodied by using the interdigitated array electrodes 66a and 66b disposed on a top substrate 1 or a bottom substrate 3 and the capture probe 43 to which a metal ball is attached in order to detect a specific binding reaction between bio materials generated on the assay site 132. Specifically, impedance can be measured in such a manner that the control unit 189 applies an alternative signal having a predetermined bandwidth from the control unit 189 to the interdigitated array electrodes 66a and 66b so as to evaluate frequency reply characteristics.

In a thin film bio valve device according to an embodiment of the inventive concept, the interdigitated array electrodes 66a and 66b may be formed by using an aluminum thin film adhesive tape or by patterning a ferromagnetic intermediate substrate into an interdigitated array shape.

According to an embodiment of the inventive concept, a control unit 189 may be provided by a wireless RF IC, or connected by a USB interface member.

Figure 17:
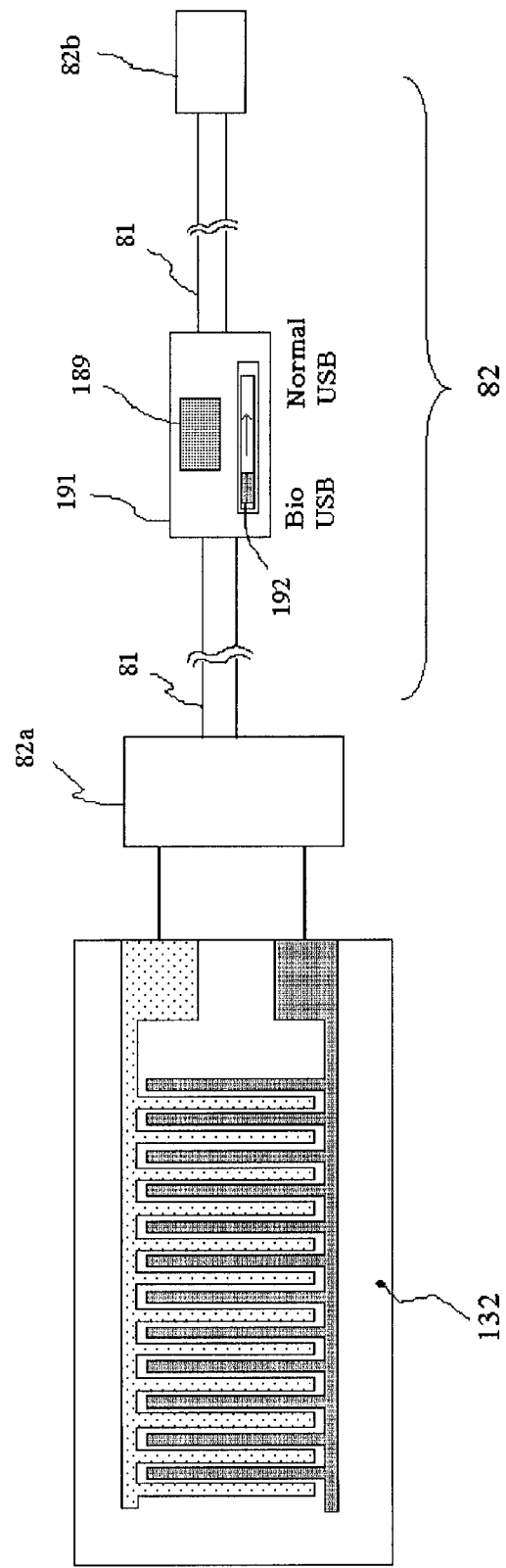
FIG. 17 illustrates a control unit connected to a USB interface member, according to an embodiment of the inventive concept.

FIG. 17 is a view illustrating a control unit 189 connected to a USB interface member 82, according to an embodiment of the inventive concept. A reference numeral 82a and a reference numeral 82b denote USB connection terminals, and a reference numeral 81 denotes a cable connecting the USB connection terminals 82a and 82b. The control unit 189 is disposed in a plastic case 191. The control unit 189 transfers a control signal for the impedance measurement device or electrochemical detection device to an assay site 132 via the USB connection terminal 82a, and transfers evaluation results to a computer via the USB connection terminal 82b. In addition, the plastic case 191 may include a switch 192 to allow the USB interface member 82 to be used as a conventional USB cable connection terminal. That is, when the USB interface member 82 is used for the impedance measurement device or electrochemical detection device, the switch 192 is set for a Bio USB state, and when the USB interface member 82 is conventionally used, the switch 192 is set for a Normal USB state.

Figure 18:
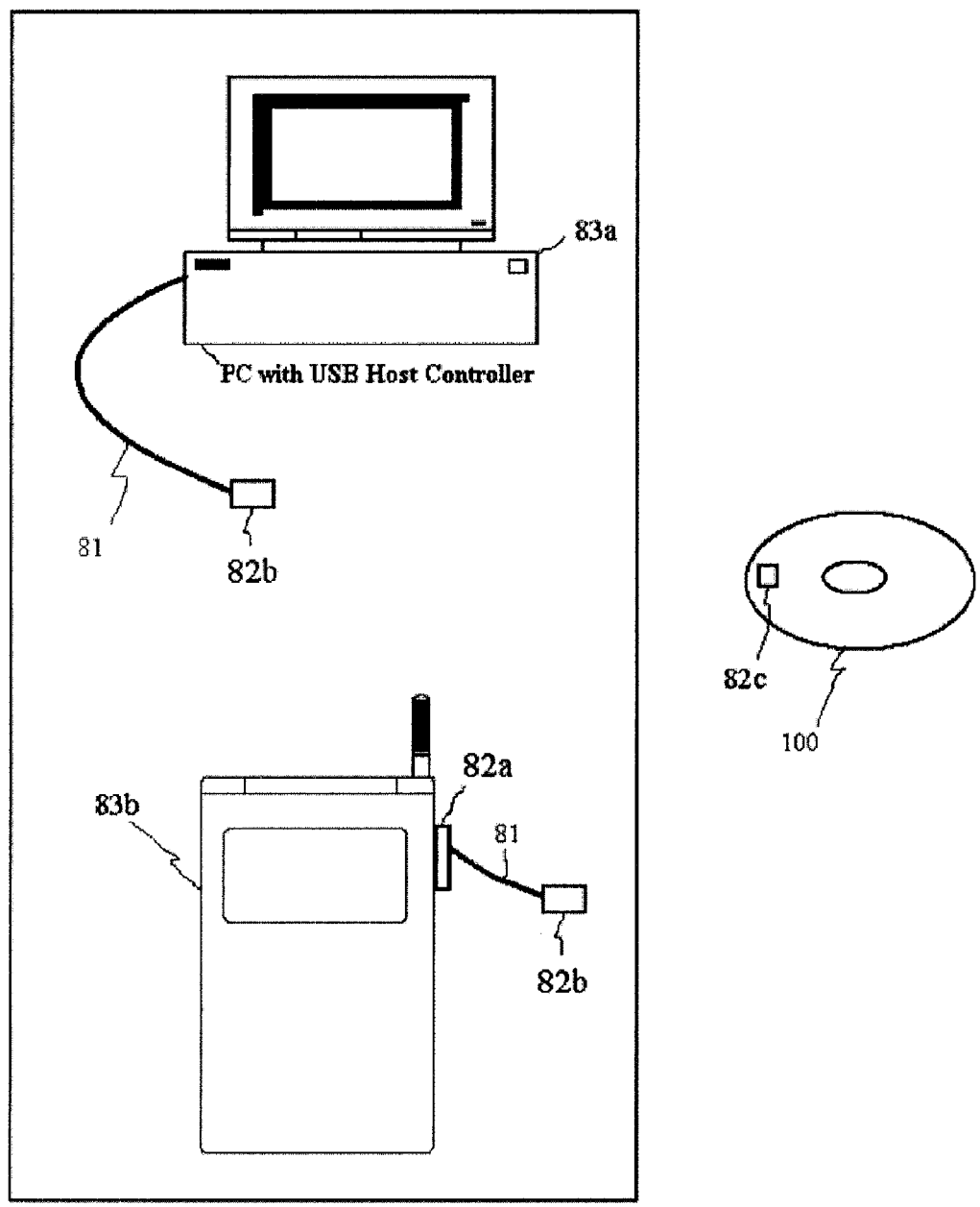
FIG. 18 illustrates a thin film bio valve device connected to a PC and/or a mobile phone by a USB interface member, according to an embodiment of the inventive concept.
Figure 20:
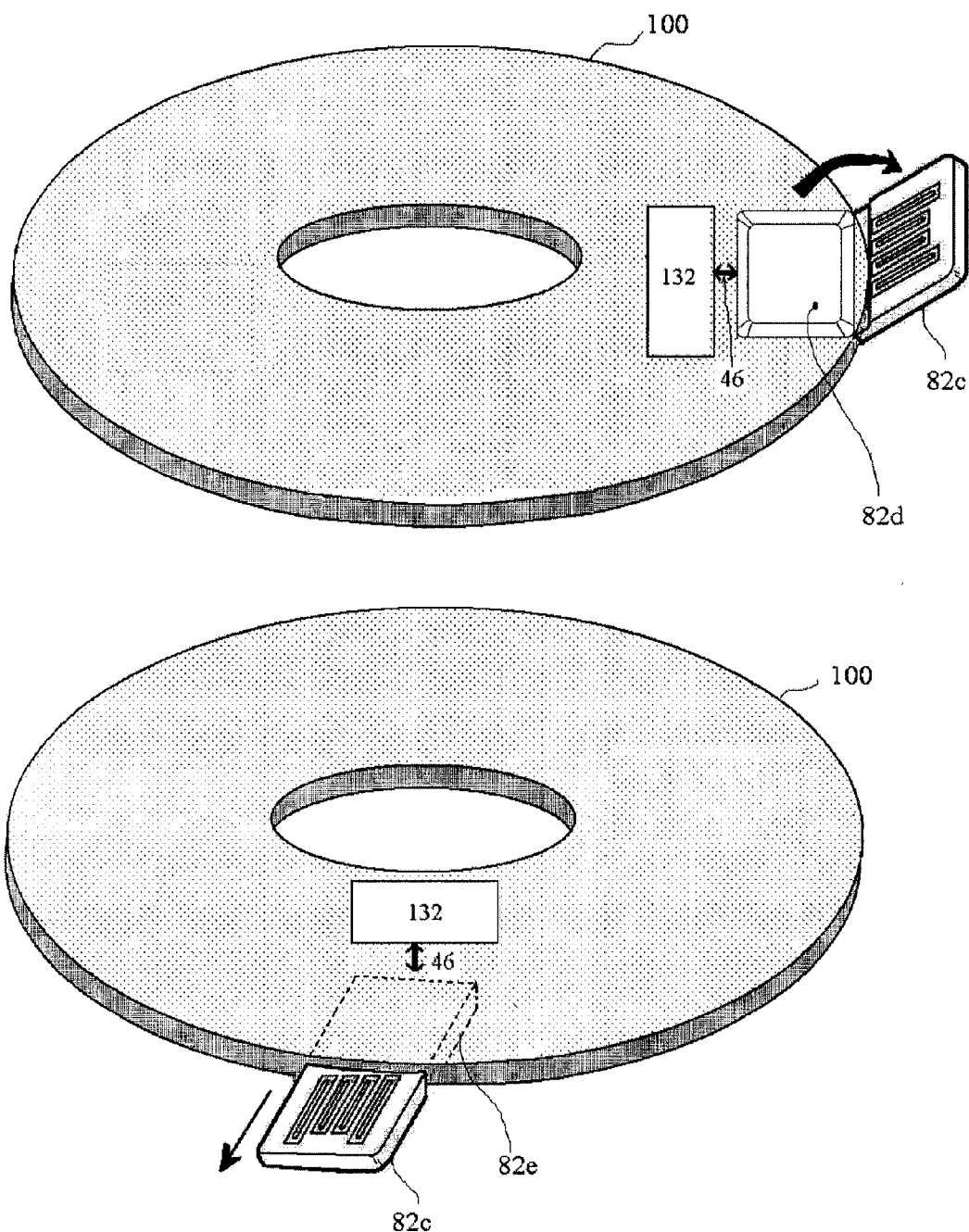

FIG. 18 illustrates a case in which a thin film bio valve device according to an embodiment of the inventive concept is connected to a PC 83a by the USB interface member or a case in which a thin film bio valve device according to an embodiment of the inventive concept is connected to a mobile phone 83b by the USB interface member 82 of FIG. 17. Due to the connection, results of the reaction in the assay site 132 are evaluated and the evaluation results can be remotely transferred. That is, the PC 83a or the mobile phone 83b may remotely transfer the evaluation results of the assay site 132 to a hospital server via the USB interface member 82 and a wired or wireless internet connection, thereby enabling remote diagnosis.

FIG. 19 illustrates a USB connection unit 82c integrated with a thin film bio valve device 100 to provide connection with respect to the USB interface member 82 illustrated in FIG. 17, according to various embodiments of the inventive concept.

FIG. 19 illustrates a USB connection unit 82c including receipt boxes 82d and 82e for receiving the USB connection unit 82c in a thin film bio valve device 100, according to an embodiment of the inventive concept.

In the thin film bio valve device 100 according to the current embodiment, an electric connection 46 between an assay site 132 and the USB connection unit 82c may be formed by using an aluminum thin film adhesive tape or by circuit-patterning a ferromagnetic intermediate substrate.

Figure 21:
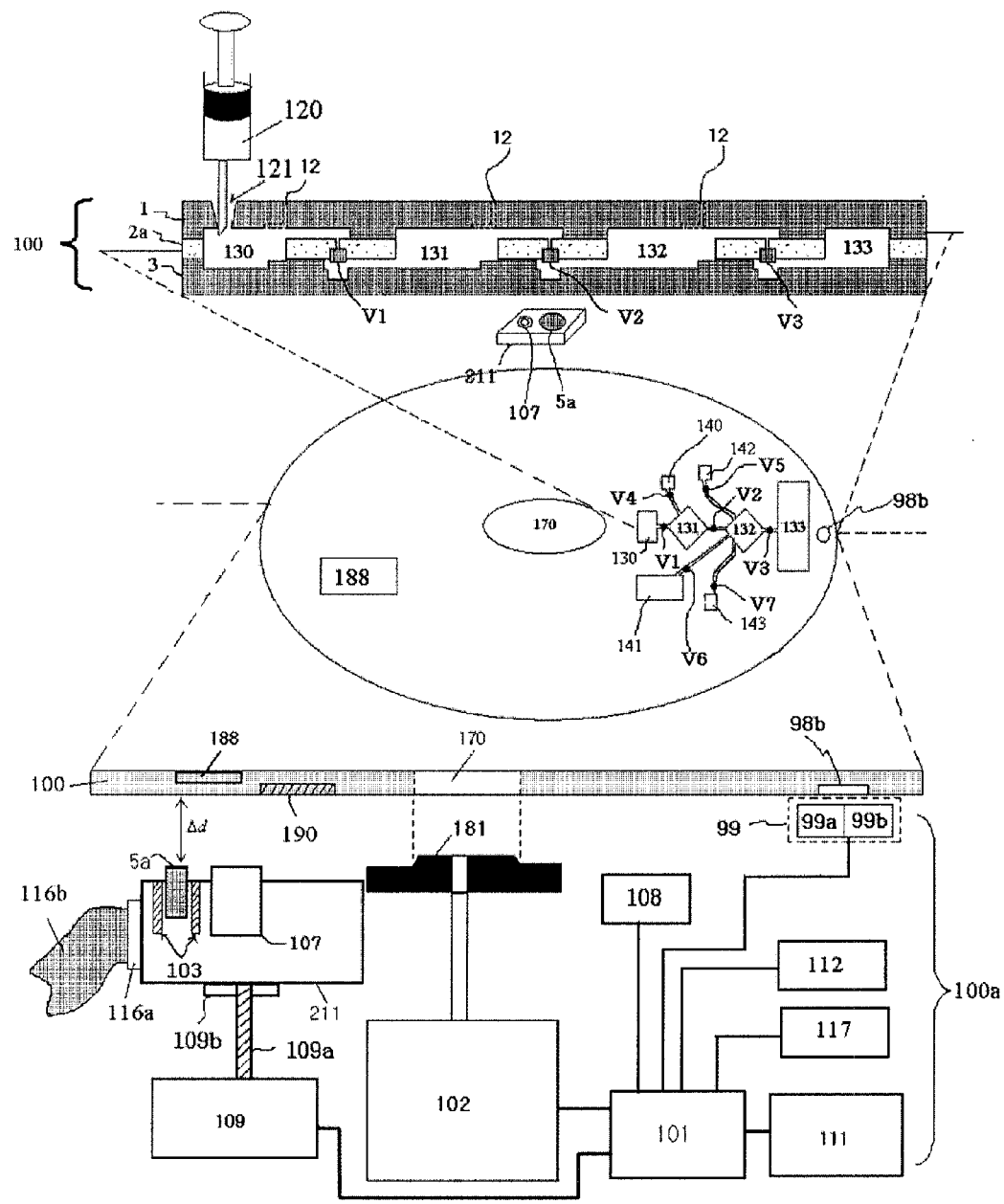

FIGS. 21 through 25 are views illustrating a thin film bio valve device according to an embodiment of the inventive concept and apparatuses 100a for controlling the thin film bio valve device according to embodiments of the inventive concept. Referring to FIG. 21, the thin film bio valve device according to the present embodiment includes chambers in which various buffer solutions needed for assays are to be contained and various chemical processes are performed; channels through which treated fluids and buffer solutions flow; channel holes connecting the channels; and a plurality of magnetic valves for opening and closing the channel holes. In addition, the apparatus for controlling a thin film bio valve 100a controls the rotation of the thin film bio valve device in which these members are integrated and the space-addressing of the movable permanent magnet 5a, in order to selectively open and close the plurality of magnetic valves. A reference numeral 100 denotes a body of a thin film bio valve device. The body 100 is formed by combining a top substrate 1, an intermediate substrate 2a, and a bottom substrate 3. In an injection molding process for forming the thin film bio valve device, the top substrate 1, t a plurality of channels through which a fluid flows along surfaces of the top substrate 1, intermediate substrate 2a, and bottom substrate 3, a plurality of chambers that are used to contain a buffer solution, and a plurality of channel holes connecting the channels are formed. The top substrate 1, the intermediate substrate 2a, and the bottom substrate 3 may be attached to each other to form the body 100. Valve operation of chambers 130, 131, 132, 133, 140, 141, 142, and 143 may be performed by using magnetic valves V1, V2, V3, V4, V5, V6, and V7 according to various embodiments of the inventive concept. In the present embodiment, the magnetic valves V1, V2, V3, V4, V5, V6, and V7 have the structure of the magnetic valve 70 illustrated in FIG. 1. Each of the magnetic valves V1, V2, V3, V4, V5, V6, and V7 is independently opened or closed due to a magnetic force generated by an intermediate substrate 2a and a movable permanent magnet 5a. A reference numeral 120 denotes a specimen injection member for injecting a sample. The specimen injection member may be a dispenser, a pipette, a syringe or a lancet. A reference numeral 121 denotes a specimen inlet, and a reference numeral 170 denotes a disk opening.

A reference numeral 130 denotes a preparation chamber in which a preparation process is performed to extract a sample from a specimen (biomaterial), a reference numeral 131 denotes a buffer chamber in which an amplification process for amplifying the sample, a mixing process for diluting or mixing the sample, or a labeling process for labeling the sample is performed, a reference numeral 132 denotes a chamber in which a molecular or biochemical reaction process is performed, that is, an array site in which a capture probe for assaying and/or diagnosing the sample contained in the buffer chamber is attached(fixed) to a substrate or can be immobilized to the substrate by using a immobilizing member, and a reference numeral 133 denotes a waste chamber for collecting waste generated after a washing process is performed. The capture probe may have an array structure to perform multiple detections with respect to a single specimen and/or sample. The assay site 132 may be formed by integrating a DNA chip, a protein chip, a bio chip, a porous membrane or a 96-well plate. The porous membrane may include a material that derives diffusion of a sample. The material that derives diffusion of a sample may be nitrocellulose (NC), a nylon membrane, or a nanotube. The assay site 132 may be used for a biochemical and/or molecular biochemical assay using 96, 384, and 1536 well plates, which is performed to screen a novel drug or a novel material, which is well known. The preparation chamber 130 may be used to extract DNA from blood, extract serum or blood plasma from blood by centrifuging the blood when the body 100 rotates at high speed, or extract agricultural products, germs, or heavy metal components from farm produce. The amplification process may be a PCR polymer chain reaction (PCR) process for amplifying DNA or a process for amplifying germs in an enrichment medium. Reference numerals 140, 141, 142 and 143 denote members for containing: an extraction solution for extracting the sample from the specimen; a dilution solution for diluting a polymerase for the amplification; various enzymes including a primer; various enzymes for hybridization, or the sample; a labeling material; a biochemical material for a biochemical reaction; a washing solution for a washing process, etc.

A reference numeral 102 denotes a spindle motor for rotating the thin film bio valve device. The reference numeral 211 denotes a slider on which a movable permanent magnet 5a is mounted. The slider 211 may be driven by a slide motor 109 and worm gear connection units 109a and 109b. For each of the processes (the preparation process, the amplification process, the mixing process, the diluting process, the labeling process, the biological and/or biochemical reaction process, and the washing process), opening and closing of the corresponding magnetic valve at the starting or ending points may be performed in such a manner that the corresponding magnetic valve is moved up and down by space-addressing the permanent magnet 5a mounted on the slider 211 with respect to the corresponding magnetic valve.

In an apparatus for controlling a thin film bio valve according to an embodiment of the inventive concept, the space-addressing with respect to the magnetic valve may be space-addressing in a radial direction or space-addressing in an azimuth direction. The space-addressing in the radial direction with respect to the magnetic valve may be realized when the slide motor 109 reversibly moves the slider in the radial direction. Due to the operation of the slider motor 109, the slider 211 moves in the radial direction in a direction from the center of the body 100 to the outside or in a direction from the outside to the center of the body 100.

In the apparatus 100a for controlling a thin film bio valve according to the current embodiment of the inventive concept, a distance Δd between the body 100 and the permanent magnet 5a may be controlled by an up-down movement member 103. The up-down movement member 103 may be physically connected to the permanent magnet 5a and a gear (now shown) and thus, the permanent magnet 5a is moved up and down according to the rotary direction of the gear. In other embodiments, the permanent magnet 5a may be moved up and down by a current control of an electromagnetic material. When the space-addressing is performed, the up-down movement member 103 moves the permanent magnet 5a downward to increase the distance between the permanent magnet 5a and the magnetic valve 70 so that the permanent magnet 5a does not magnetically affect the magnetic valve 70. When the space-addressing is completed, the up-down movement member 103 moves the permanent magnet 5a upward to reduce the distance between the permanent magnet 5a and the magnetic valve 70 so that the permanent magnet 5a magnetically affects the magnetic valve 70.

In the apparatus 100a for controlling a thin film bio valve according to the current embodiment of the inventive concept, an optical pick-up device (CD or DVD reader) 107 may be further mounted on the slider 211. The optical pick-up device is used to read a conventional optical disk, such as a music CD, CD-R, game CD, or DVD.

A reference numeral 116b denotes a flexible cable for supplying various control signals for the up-down movement member 103 and optical pick-up device 107 of the slider 211. The flexible cable 116b is connected to a central control device 101 via a wafer or harness 116a. A reference numeral 181 denotes a turntable on which the thin film bio valve device is disposed. The thin film bio valve device is placed on the turntable 181 via the disk opening 170 while a front or top of the thin film bio valve device faces the turn table 170. A reference numeral 188 denotes a wireless RF IC that includes a built-in memory. The wireless RF IC 188 includes a protocol for the thin film bio valve device, an assay algorithm, a standard control value for reading and/or information about location of an assay site, bioinformatics information, and information about self diagnosis. The wireless RF IC 188 may also include personal encryption information and/or ID identification of a thin film bio valve device to prevent use of other people. The wireless RF IC 188 may be a smart IC card. Information contained in the wireless RF IC 188 may be provided to the central control device 101 by wireless communication, and may be used for personal encryption. A reference numeral 117 denotes a wireless radio wave generation unit for supplying power to the wireless RF IC 188. Radio waves generated by the wireless radio wave generation unit 117 activate an electron induction coil installed in the wireless RF IC 188 according to Fleming's rule and produce a sufficient amount of electricity and provide the power to the wireless RF IC 188.

The thin film bio valve may further include a solar cell 190 for providing power to the wireless RF IC 188.

The apparatus for controlling a thin film bio valve according to the current embodiment may further include an illuminating device 108 for supplying light energy to the solar cell 190 disposed in the thin film bio valve device. The illuminating device 108 may be a high luminance LED module or lamp in which a plurality of high luminance LEDs are integrated in a module structure.

In the apparatus for controlling a thin film bio valve according to the current embodiment, when the thin film bio valve device is installed, a unique ID of the thin film bio valve device is wirelessly transmitted to the central control device 101 by the wireless RF IC 188, so that the central control device 101 recognizes that a disk that is currently loaded in the apparatus for controlling a thin film bio valve 100a is the thin film bio valve device.

The apparatus for controlling a thin film bio valve according to the current embodiment may further include an input-output device 111.

The apparatus for controlling a thin film bio valve according to the current embodiment may further include a plurality of USB ports 112 that are to be connected to a computer. The USB port 112 may be connected to a computer peripheral to provide an interface with respect to a computer. Examples of the computer peripheral include a camera, a keyboard, earphones, a mouse, a memory stick, an electronic stethoscope, a sphygmomanometer, an electronic thermometer, and a pharmaceutical measuring instrument.

In the apparatus for controlling a thin film bio valve according to the current embodiment, the input-output device 111 may have a communications standard of a universal serial bus (USB), IEEE1394, ATAPI, SCSI, IDE, or a wired or wireless internet connection. A reference numeral 99 refers to an optical detector.

FIG. 22 illustrates the optical detector 99 according to an embodiment of the inventive concept. If the optical detector 99 is a transmission-type optical detector, whenever photo couplers 99a and 99b face a reference hole 98a formed in the body 100 when the body 100 rotates, the optical detector 99 generates a reference trigger signal and transfers the reference trigger signal to the central control device 101. If the optical detector 99 is a reflection-type optical detector, whenever a photo coupler 99a and 99b face a reference reflector 98b formed in the body 100 when the body 100 rotates, the optical detector 99 generates a reference trigger signal and transfers the reference trigger signal to the central control device 101. The central control device 101 sets a zero degree of azimuth based on the reference trigger signal. An azimuth reference coordinate of the azimuth turn-table or azimuth search motor may be set based on the zero degree of azimuth.

Figure 23:
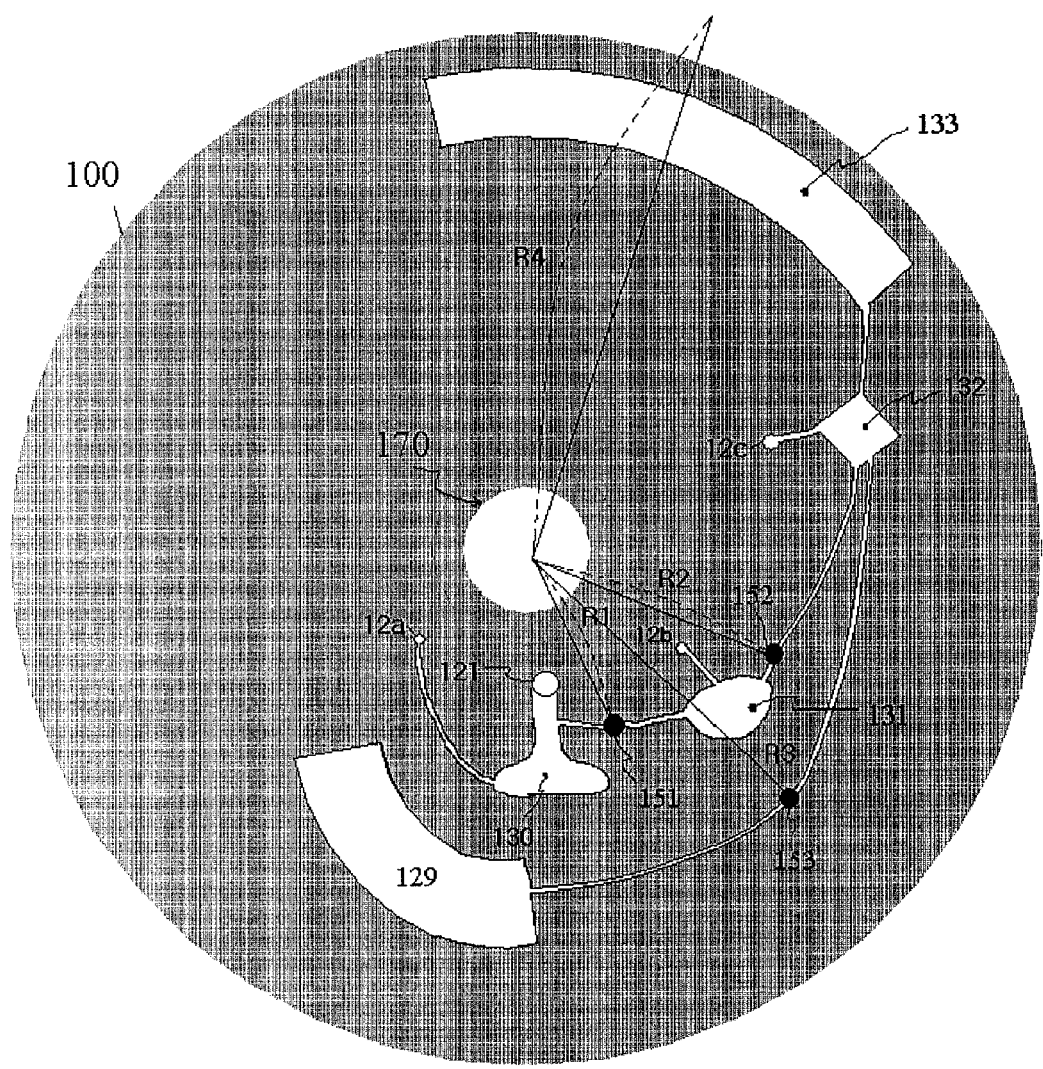

FIG. 23 is a view to explain the space-addressing with respect to magnetic valves 151, 152 and 153, and an operation of the "pulse valve." A reference numeral 100 denotes a body of a thin film bio valve device. Chambers 129, 130, 131, 132, and 133 may be driven by an up and down movement, clockwise and/or anticlockwise movement, or radial movement of the magnetic valves 151,152, and 153. A reference numeral 121 denotes an inlet through which a specimen is supplied, and a reference numeral 170 denotes a disk opening. A reference numeral 130 denotes a preparation chamber in which a preparation process is performed to extract a sample from a specimen (biomaterial). A reference numeral 131 denotes a buffer chamber in which an amplification process for amplifying the sample, a mixing process for diluting or mixing the sample, or a labeling process for labeling the sample is performed. A reference numeral 132 denotes a chamber in which a molecular or biochemical reaction process is performed, that is, an array site in which a capture probe for assaying and/or diagnosing the sample contained in the buffer chamber is attached to a substrate or immobilized to the substrate by using an immobilizing member. A reference numeral 129 denotes a washing chamber containing a washing solution. A reference numeral 133 denotes a waste chamber for collecting waste generated after the washing process is performed.

Reference numerals 12a, 12b and 12c denote vents. For each of the processes (the preparation process, the amplification process, the mixing process, the diluting process, the labeling process, the biological and/or biochemical reaction process, and the washing process), opening and closing of the corresponding magnetic valve at the starting or ending points may be performed by space-addressing the permanent magnet 5a mounted on the slider 211 with respect to the corresponding magnetic valve. The space-addressing may be space-addressing in a radial direction, or the space-addressing may include a space-addressing in a radial direction and a space-addressing in an azimuthal direction.

Referring to FIG. 23, R1 denotes a distance between the center of the body 100 and the magnetic valve 151, R2 denotes a distance between the center of the body 100 and the magnetic valve 152, R3 denotes a distance between the center of the body 100 and the magnetic valve 153, and R4 denotes a distance between the center of the body 100 and the outside of the body 100, wherein R1<R2<R3<R4. For the space-addressing in the radial direction, the movable permanent magnet 5a is moved in the radial direction. That is, the movable permanent magnet 5a is moved in the radial direction away from the center of a channel hole to the corresponding radius R1, R2 or R3. For example, to perform space-addressing with respect to the magnetic valve 151, the slider 211 is space-addressed in the radial direction to a location corresponding to R1; and to perform space-addressing with respect to the magnetic valve 152, the slider 211 is space-addressed in the radial direction to a location corresponding to R2. Then, the space-addressing in the azimuth direction is required to match the permanent magnet 5a with the corresponding magnetic valve at the corresponding radius. The space-addressing in the azimuth direction may be performed by slowly rotating the spindle motor 102 while the slider 211 is stopped, or by repeatedly performing a cycle of short-rotating and stopping the spindle motor 102. When the permanent magnet 5a mounted on the slider 211 is matched with the corresponding magnetic valve at the corresponding radius by slowly rotating the spindle motor 102 or repeatedly performing short-rotating, an adhesive force is generated between the permanent magnet 5a and the corresponding magnetic valve and thus, the body 100 of the thin film bio valve device is not rotated any more by the slow-rotation and short-rotation. That is, the permanent magnet 5a is matched with the corresponding magnetic valve by the space-addressing in the radial direction and the space-addressing in the azimuth direction, and thus, the space-addressing in the azimuth direction, in addition to the space-addressing in the radial direction, is completed. The "pulse valve" may be driven when the body 100 is rotated by the space-addressing in the radial direction. For example, to open the magnetic valve 151 by the pulse valve operation, the permanent magnet 5a mounted on the slider 211 is moved to a location corresponding to R1, and then the body 100 is rotated. When the body 100 rotates, the magnetic valve 151 faces the movable permanent magnet 5a and, whenever the magnetic valve 151 faces the movable permanent magnet 5a, an attractive force is generated between the magnetic valve 151 and the movable permanent magnet 5a, thereby instantly opening a channel hole that has been closed by the magnetic valve 151. In addition, since the body 100 rotates, whenever the channel hole that has been closed by the magnetic valve 151 is opened, a fluid moves due to a centrifugal force. To close the channel hole during the pulse valve operation, the movable permanent magnet 5a is moved to R4. In this case, the movable permanent magnet 5a located at R4 does not affect the magnetic valves 151, 152, and 153, and the channel hole is closed due to an attractive force between the intermediate substrate (see 2a of FIG. 1) and the magnetic valve 151.

Figure 24:
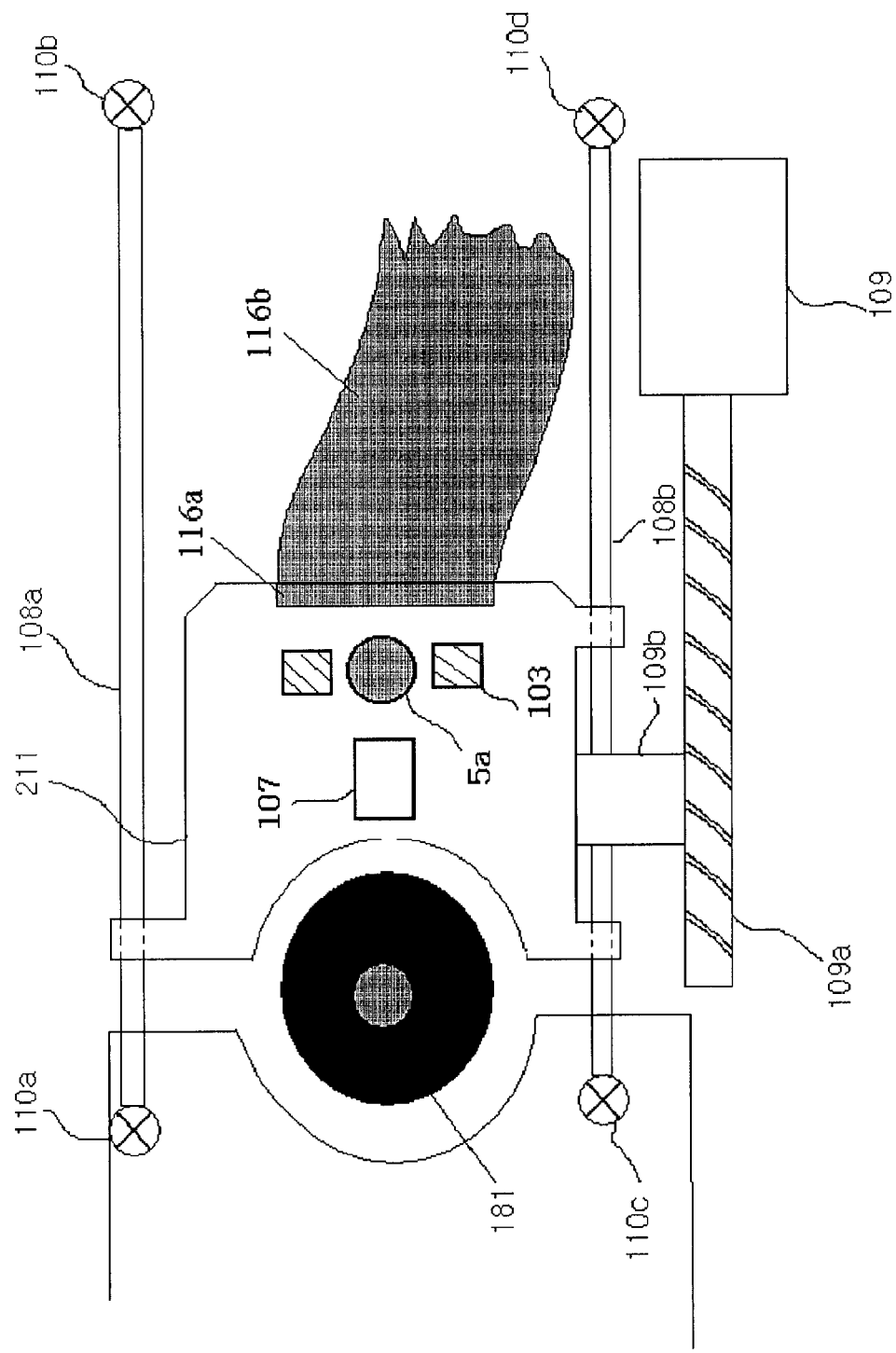

FIG. 24 illustrates the slider 211 in which the optical pickup device 107, the movable permanent magnet 5a, and the up-down movement member 103 are integrated, according to an embodiment of the inventive concept. Movement of the slider 211 is controlled by the worm gear connection units 109a and 109b connected to the slide motor 109. The slider 211 slides by using slide arms 108a and 108b as a guide. The slide arms 108a and 108b are formed in a body of the apparatus for controlling a thin film bio valve through screws 110a, 110b, 110c, and 110d. The reference numeral 116b denotes a flexible cable. The flexible cable 116b is connected to the central control device 101 by connection with the wafer or harness 116a. The reference numeral 181 denotes a turntable that is rotated by the spindle motor 102.

Figure 25:
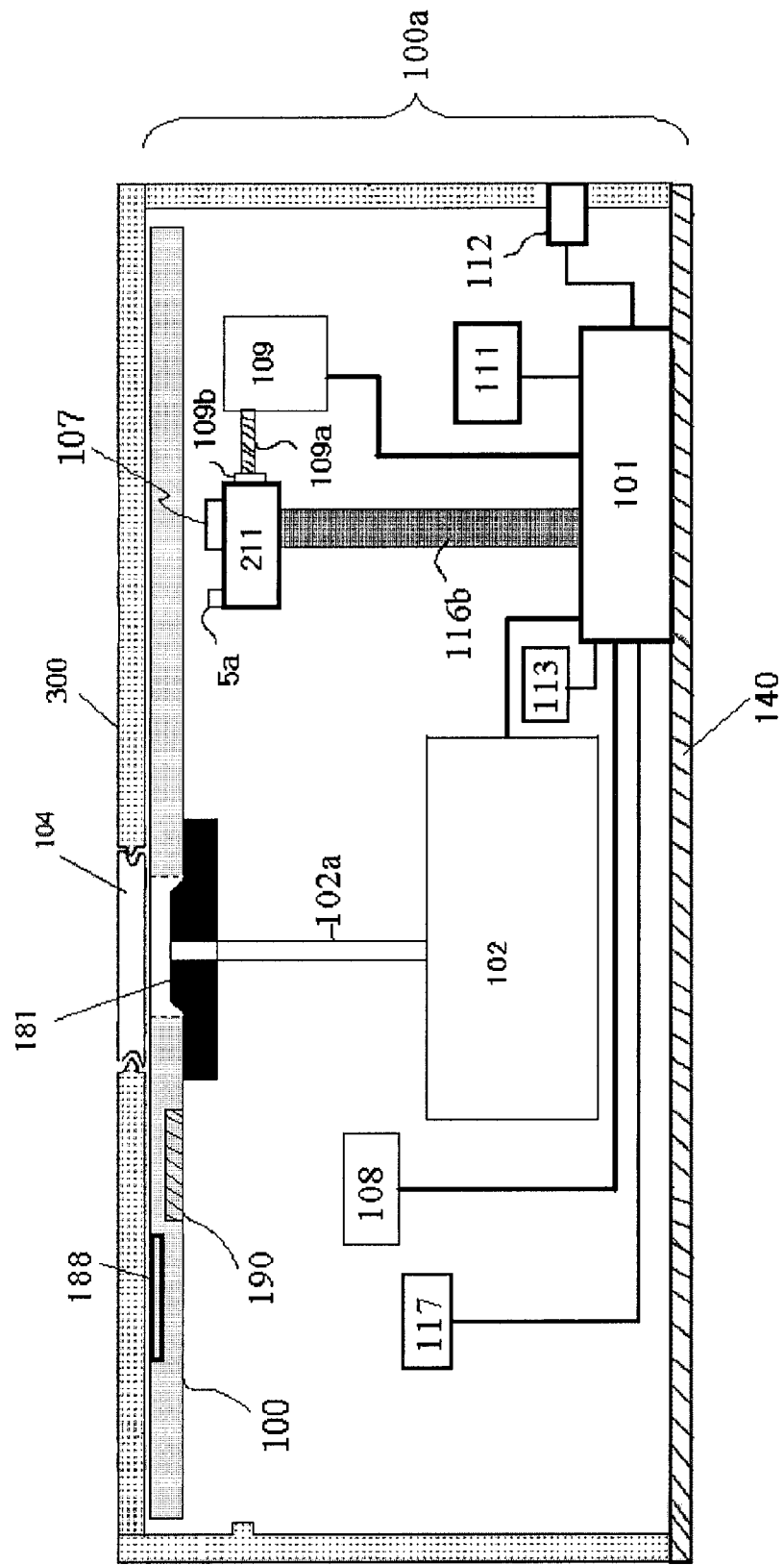

FIG. 25 illustrates an apparatus for controlling a thin film bio valve 100a for opening and closing a magnetic valve of a thin film bio valve device, according to an embodiment of the inventive concept.

Referring to FIG. 25, a reference numeral 300 denotes a body that supports the apparatus for controlling a thin film bio valve 100a. A circuit substrate 140 is joint-tightened with respect to the body 300 of the apparatus for controlling a thin film bio valve 100a and forms a bottom surface of the apparatus for controlling a thin film bio valve 100*a*. The central control device 101 for controlling the apparatus for controlling a thin film bio valve 100*a*, the wireless radio wave generation unit 117, the illuminating device 108, and the input-output device 111 are designed and deployed on the circuit substrate 140. The central control device 101 controls the spindle motor 102 for rotating or stopping the thin film bio valve device 100*a*. Also, by controlling the slide motor 109, the central control device 101 also controls the optical pick-up device 107 and the movable permanent magnet 5*a* which are designed and deployed on the slider 211.

A reference numeral 104 denotes a compression member for compressing the thin film bio valve device 100*a* loaded via a disk opening. Specifically, the compression member 104 may be an idle rotary table that is to be compressed due to a magnetic attraction with respect to the turntable 181. The idle rotary table 104 may be designed to allow a vertical movement and an idle rotation. Specifically, in an embodiment of the inventive concept, an intermediate substrate (see 2*a* of FIG. 1) may be formed by using a ferromagnetic material to generate an attractive force caused by a magnetic force between the intermediate substrate 2*a* and the turntable 181 or between the intermediate substrate 2*a* and the idle rotary table 104. In addition, the central control device 101 determines that a disk currently loaded in the apparatus for controlling a thin film bio valve 100*a* is either a conventional optical disk, such as a music CD, CD-R, game CD, or DVD, or a thin film bio valve device. If the currently loaded disk is a conventional optical disk, a conventional operation of an optical disk is performed. For example, information read from the disk is transmitted from the optical pick-up device 107 to a storage device 113 or the input-output device 111, or information to be written is transmitted to the optical pick-up device 107, and then various control signals for a Read/Write operation are provided to respective members described above. If the currently loaded disk is the thin film bio valve device 100*a*, an operation for controlling a bio process and/or a chemical process is performed.

FIGS. 26 through 29 illustrate an apparatus for controlling a thin film bio valve using an actuator 80, according to various embodiments of the inventive concept. Referring to FIGS. 26 through 29, a scan magnet 5*b* is fixed to a front end of the actuator 80. A pivot 87 that is a rotary center of the actuator 80 is disposed on a side surface of a middle portion of the actuator 80. The pivot 87 includes a pivot screw and a pivot bearing. A voice coil 86 is wound many times on a bobbin 84 formed of a plastic material, and is disposed on another side surface of the actuator 80. The voice coil 86 is used to turn the scan magnet 5*b* of the actuator 80 to a specific location on the thin film bio valve device 100. An iron piece 88 is disposed on an end of the bobbin 84.

Figure 26:
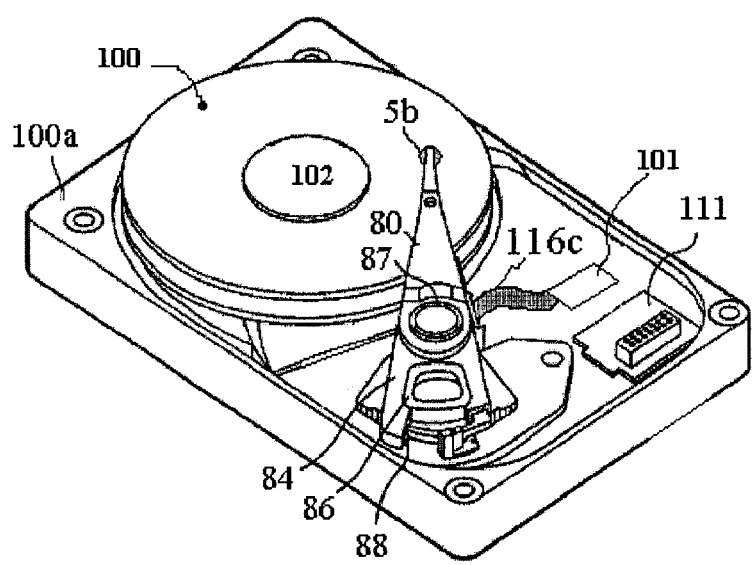
FIGS. 26 through 29 are diagrams of thin film bio valve control devices using an actuator, according to various embodiments of the inventive concept.

FIG. 26 illustrates an apparatus for controlling a thin film bio valve that opens a channel hole by using the actuator 80 and the scan magnet 5*b*, according to an embodiment of the inventive concept. The channel hole is closed due to an attractive force between a top permanent magnet and a magnetic valve or an attractive force between an intermediate substrate and the magnetic valve. The scan magnet 5*b* is mounted on the actuator 80, and is space-addressed in a radial direction and an azimuth direction with respect to a magnetic valve to be closed or opened and thus generates an attractive force with respect to the magnetic valve, thereby opening the channel hole. For the space-addressing in the radial direction, the actuator 80 is turned with respect to the pivot 87 according to the central control device 101, and during the turning, the scan magnet 5*b* fixed on the front end of the actuator 80 is moved to a desired location on the thin film bio valve device 100. Then, the space-addressing in the azimuth direction is performed. For the space-addressing in the azimuth direction, after the space-addressing in the radial direction is completed, while the actuator 80 is stopped, the spindle motor (see 102 of FIG. 25) is slowly rotated or a cycle including short-rotating and/or stopping the spindle motor 102 is repeatedly performed. When the scan magnet 5*b* is matched with a magnetic valve at the corresponding radius by slowly rotating the spindle motor 102 or repeatedly performing short-rotating, an adhesive force is generated between the scan magnet 5*b* and the corresponding magnetic valve and thus, the body 100 of the thin film bio valve device is not rotated any more by the slow-rotation and short-rotation. Accordingly, the space-addressing in the azimuth direction with respect to the channel hole to be opened or closed is completed.

In a thin film bio valve-controlling device according to another embodiment of the inventive concept, actuators are simultaneously disposed on and under the thin film bio valve device, and space-addressing is performed on the same location of the thin film bio valve device. In this case, the closing of a channel hole may be performed due to an attractive force between an intermediate substrate and a magnetic valve, and the opening of the channel hole may be performed due to a combined magnetic force of a repulsive force between a scan magnet mounted on the upper actuator and the magnetic valve and an attractive force between a scan magnet mounted on the lower actuator and the magnetic valve. That is, a strong magnetic force affects the magnetic valve. If many magnetic valves are needed to be integrated into a thin film bio valve device, the size of each of the magnetic valves is decreased. In this case, the strength of the magnetic force of the magnetic valves is decreased. Accordingly, to move these magnetic valves, a stronger outer magnetic force is needed. In this case, an apparatus for controlling a thin film bio valve using upper and lower actuators generates a strong magnetic force and applies the strong magnetic force to a magnetic valve. Thus, the film bio valve-controlling apparatus using upper and lower actuators may be used to manufacture a small-sized magnetic valve. A reference numeral 116*c* denotes a flexible cable for supplying various control signals for driving the actuator 80, and is connected to the central control device 101 by a wafer or harness. A reference numeral 111 denotes an input-output device.

Figure 27:
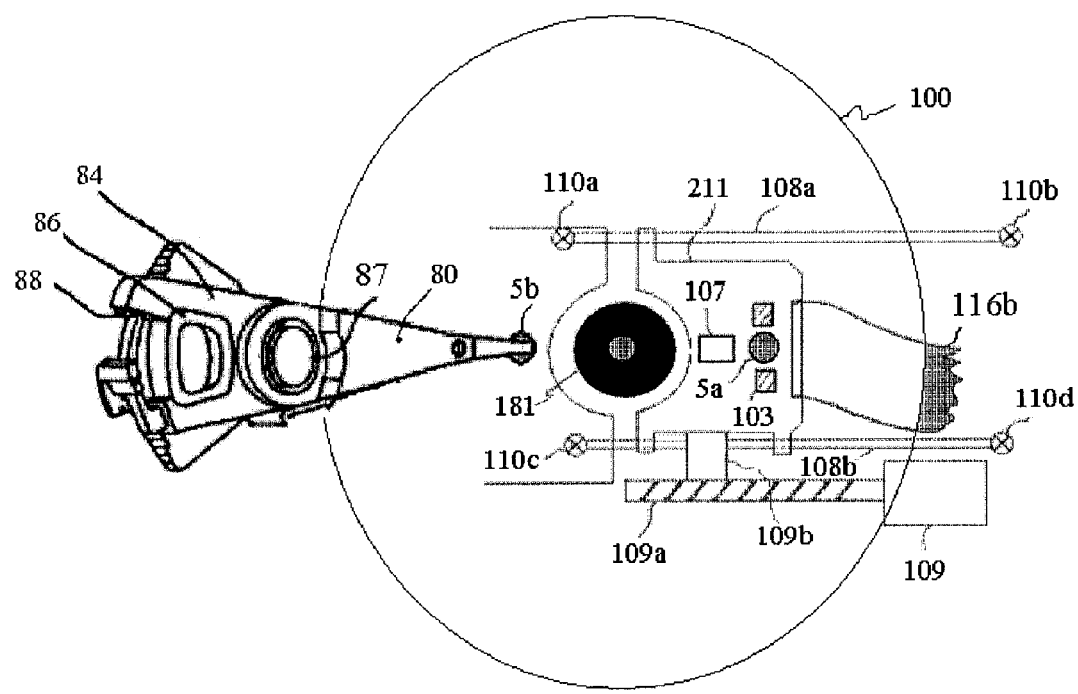

FIG. 27 illustrates an apparatus for controlling a thin film bio valve according to an embodiment of the inventive concept. Referring to FIG. 27, space-addressing in a radial direction is performed by a slider 211 on which a movable permanent magnet 5*a* is mounted, and space-addressing in an azimuth direction is performed by an actuator 80 on which a scan magnet 5*b* is mounted. The space-addressing in the radial direction may be performed by moving the slider 211 in the radial direction to a radius of the corresponding magnetic valve, after the space-addressing in the azimuth direction is completed by the actuator 80.

Figure 28:
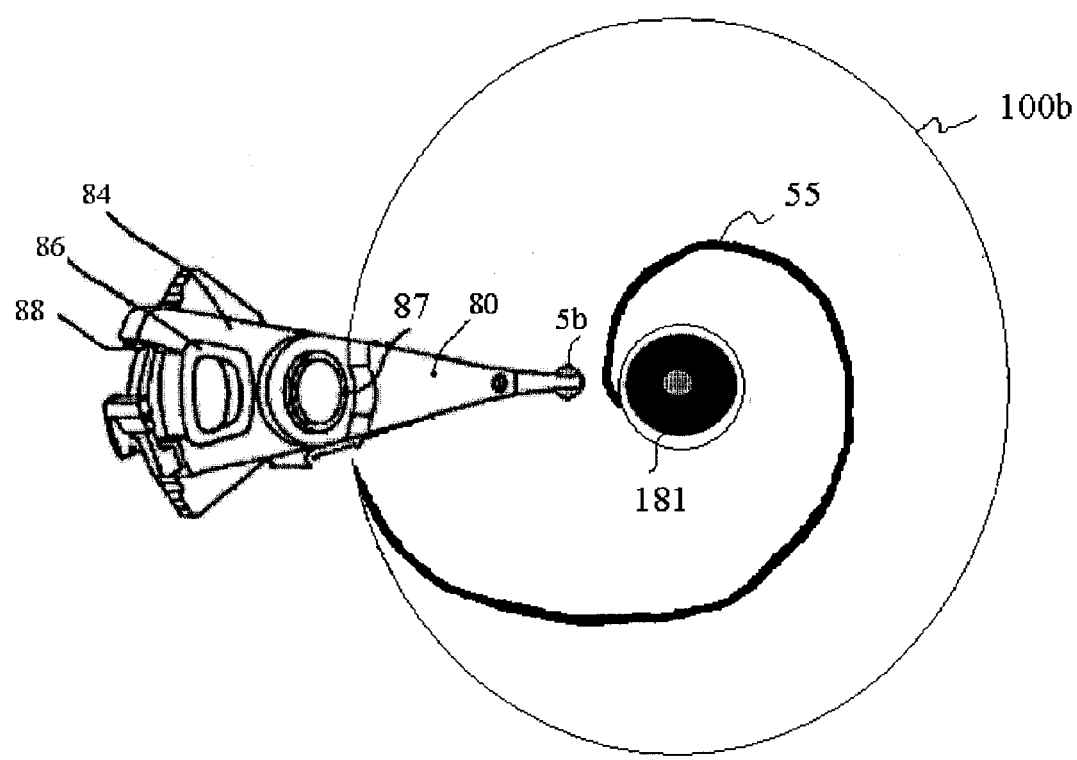
Figure 29:
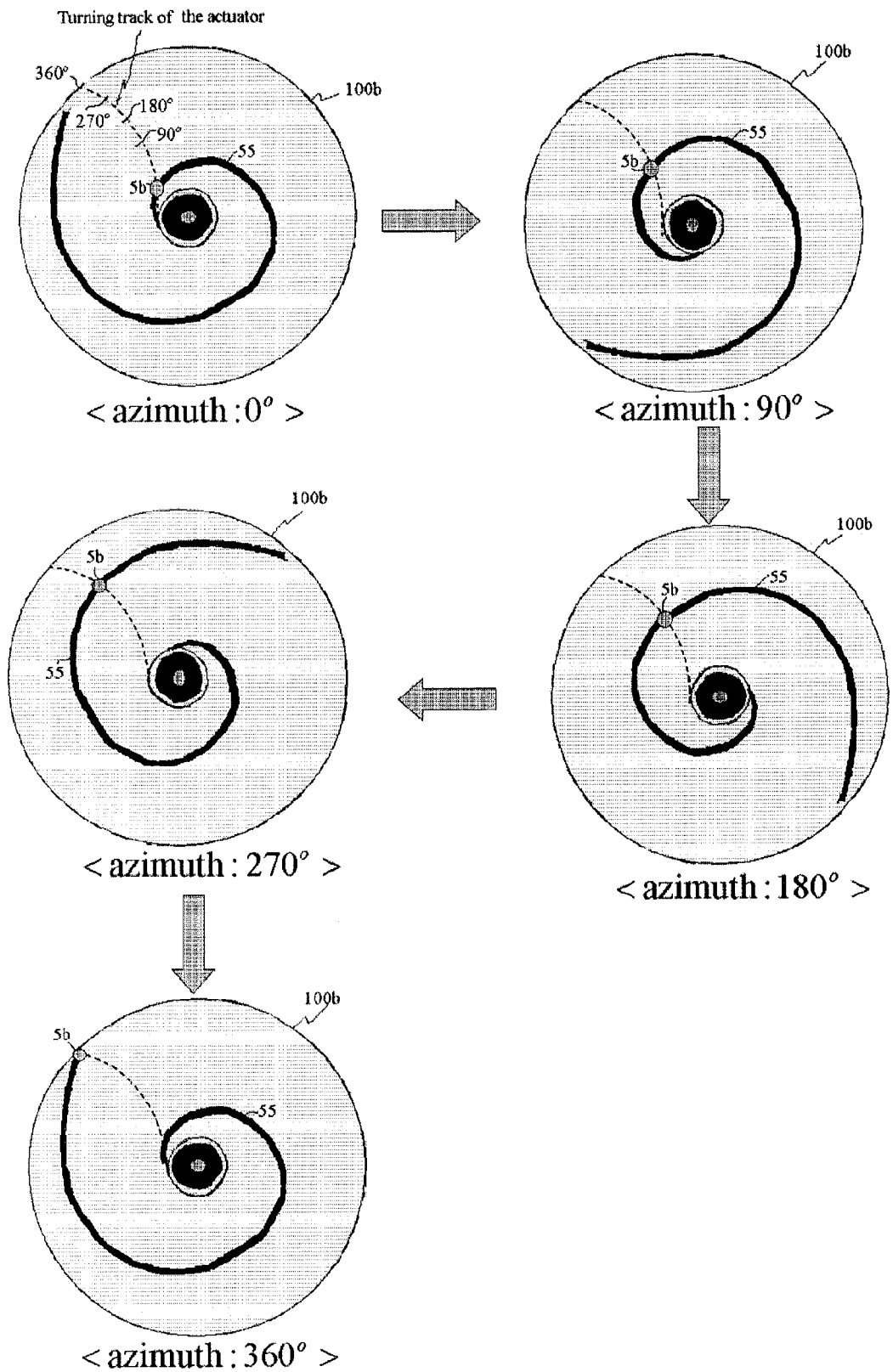

FIGS. 28 and 29 are diagrams for explaining the space-addressing in the azimuth direction by using an actuator 80 and an azimuth turntable 100*b*, according to an embodiment of the inventive concept. A spiral magnetic pattern 55 corresponding to an azimuth coordinate is disposed on the azimuth turntable 100*b*.

According to an embodiment of the inventive concept, the azimuth turntable 100*b* may be integrated with a top surface of the thin film bio valve device 100 or fixed to a rotary axis of the spindle 102. The space-addressing in the azimuth direction may be performed in such a manner that the actuator 80 is turned to a coordinate of a spiral magnet pattern corresponding to an azimuth to be addressed, and then a spindle motor is slowly rotated or a cycle including short-rotating or stopping of the spindle motor is repeatedly performed. When the scan magnet 5*b* mounted on a front end of the actuator 80 is matched with the spiral magnetic pattern 55 by the slow-rotation and short-rotations of the spindle motor, a strong adhesive force is generated between the scan magnet 5*b* and the spiral magnetic pattern 55 and thus, a body 100 of the thin film bio valve device is not rotated any more by the slow-rotation and short-rotation.

Referring to FIG. 29, coordinates of a spiral magnetic pattern to perform space-addressing azimuth 0°, 90°, 180°, 270° and/or 360° are illustrated on a turning track of an actuator. The scan magnet 5*b* is located at a coordinate of the spiral magnet pattern and the azimuth turn-table 100*b* is short-rotated. As a result, the scan magnet 5*b* is matched with the spiral magnetic pattern 55 and a body 100 of the thin film bio valve device is stopped due to a strong attraction between the scan magnet 5*b* and the spiral magnetic pattern 55. An azimuth offset of the spiral magnet pattern 55 may be determined while reference holes (see 98*a* and 98*b* of FIG. 22) are set as a zero degree.

Figure 30:
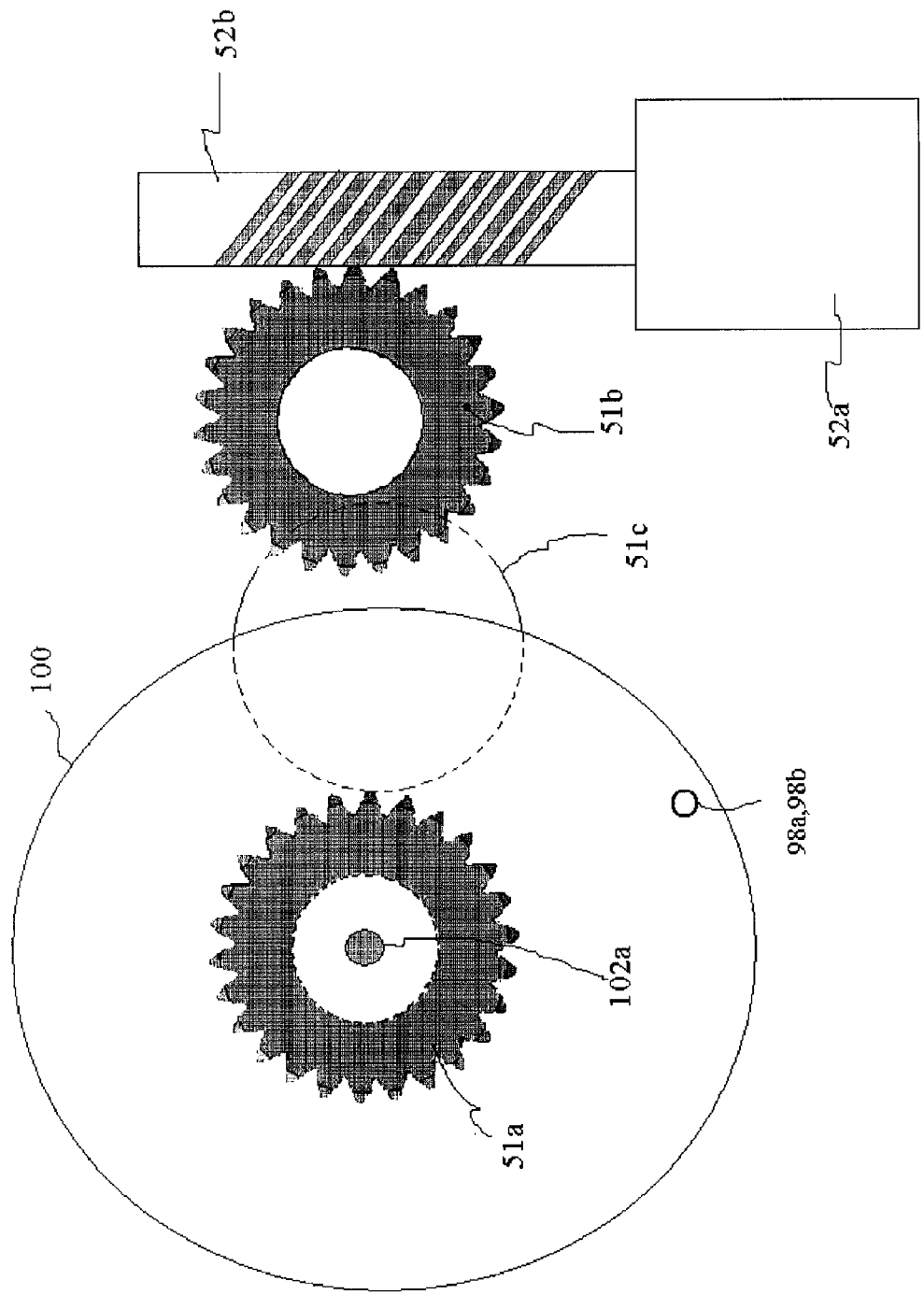
FIG. 30 is a diagram of an apparatus for controlling a thin film bio valve according to an embodiment of the inventive concept, wherein space-addressing in an azimuth direction is performed by rotating a spindle motor according to rotation of an azimuth search motor, wherein the spindle motor is rotated according to rotation of the azimuth search motor by the azimuth search motor and a gear connection member.

FIG. 30 illustrates an apparatus for controlling a thin film bio valve, according to an embodiment of the inventive concept, wherein space-addressing in an azimuth direction is performed in such a manner that a spindle motor (see 210 of FIG. 21) is rotated by an azimuth search motor 52*a* and a gear connection member according to rotation of the azimuth search motor 52*a*. The azimuth search motor 52*a* may be a stepping motor. When the space-addressing in the azimuth direction is performed, the azimuth search motor 52*a* may be connected to a rotary axis 102*a* of the spindle motor by the gear connection member, and when the space-addressing in the azimuth direction is not performed, the azimuth search motor 52*a* may be separated from the rotary axis 102*a* of the spindle motor. The gear connection member may include a gear unit 1 51*a* that is fixed and connected to the rotary axis 102*a* of the spindle motor, and a gear unit 2 51*b* that is fixed and connected to a rotary axis of the azimuth search motor 52*a*, wherein the gear unit 1 51*a* is connected to or separated from the gear unit 2 51*b* according to a rotary direction of the azimuth search motor 52*a*. The gear unit 2 51*b* may further include a worm gear 52*b* connected to the rotary axis of the azimuth search motor 52*a* and a CAM 51*c*. An azimuth offset of the azimuth search motor 52*a* may be determined while reference holes 98*a* and 98*b* are set as a zero degree.

While the inventive concept has been particularly shown and described with reference to exemplary embodiments thereof, it will be understood that various changes in form and details may be made therein without departing from the spirit and scope of the following claims.

The invention claimed is:

1. A thin film bio valve device comprising:
    at least one chamber for storing a fluid that is used for a biomaterial assay or a biochemical assay or for performing a biological or biochemical reaction;
    a specimen inlet for loading a specimen;
    a channel that connects the at least one chamber to allow the fluid to flow;
    a channel hole that is disposed at the center of the channel and connected to the channel;
    a magnetic valve for opening and closing the channel hole;
    a top substrate, an intermediate substrate and a bottom substrate in which the channel, the channel hole and the chamber are formed;
    a body in which the channel, the channel hole, the chamber, the specimen inlet, and the magnetic valve are integrated by stacking and binding the top substrate, the intermediate substrate and the bottom substrate; and
    a movable permanent magnet or scan magnet for opening the channel hole,
    wherein the channel hole is opened or closed by reversibly moving the magnetic valve in a clockwise or counter-clockwise direction due to an attractive force generated between the magnetic valve and the movable permanent magnet or an attractive force generated between the magnetic valve and the scan magnet.

2. The thin film bio valve device of claim 1, wherein the channel hole is closed due to an attractive force between the magnetic valve and the intermediate substrate or an attractive force between the magnetic valve and a fixed top permanent magnet disposed above the channel hole.

3. The thin film bio valve device of claim 1, wherein the scan magnet and movable permanent magnet have a shape selected from the group consisting of circular, cylindrical and tetragonal.

4. The thin film bio valve device of claim 1, wherein the magnetic valve comprises one selected from the group consisting of a ferromagnetic material, a thin film circular magnet, a thin film cylindrical magnet, a thin film tetragonal magnet, and a ball magnet.

5. The thin film bio valve device of claim 1, wherein the magnetic valve is coated with a silicone rubber-based rubber cushion material, or a thin film rubber is inserted between the magnetic valve and the channel hole.

6. The thin film bio valve device of claim 5, wherein the magnetic valve is moved into a slide-out space due to a centrifugal force generated when the body is rotated.

7. The thin film bio valve device of claim 1, wherein the channel hole has a circular groove on a channel hole contact portion.

8. The thin film bio valve device of claim 1, wherein the intermediate substrate comprises a plastic disk coated with a magnetic material or an aluminum disk coated with a magnetic material, or comprises a material selected from the group consisting of a permanent magnet, a ferromagnetic material, iron, cobalt, chrome, nickel and alloys thereof.

9. The thin film bio valve device of claim 1, wherein the intermediate substrate has an electric circuit pattern formed by using a mask pattern.

10. The thin film bio valve device of claim 1, wherein the chamber comprises:
    a preparation chamber for extracting a sample from a specimen;
    a buffer chamber in which an amplification process for amplifying the sample, a mixing process for diluting or mixing the sample, or a labeling process for labeling the sample is performed;
    an array site in which a capture probe for assaying and/or diagnosing the sample is fixed or can be immobilized by a immobilizing member, and
    a waste chamber for collecting waste generated after a washing process is performed.

11. The thin film bio valve device of claim 10, wherein the capture probe is formed to have an array structure in order to perform multiple detections with respect to the specimen and the sample.

12. The thin film bio valve device of claim 10, wherein the assay site is formed by integrating a DNA chip, a protein chip, a biochip, a porous membrane, or a well plate.

13. The thin film bio valve device of claim 1, wherein the channel is a thin film channel formed from a thin film adhesive tape for binding the top substrate, the intermediate substrate and the bottom substrate.

14. The thin film bio valve device of claim 1, wherein the body further comprises a holding groove or a vent.

15. The thin film bio valve device of claim 14, wherein the channel comprises a thin film channel, and an outer channel hole functions as the holding groove.

16. The thin film bio valve device of claim 1, wherein the stacking and/or binding of the top substrate, the intermediate substrate and the bottom substrate is performed in such a manner that double-sided tape is attached to the top substrate, the intermediate substrate and the bottom substrate and then a protective strip of the double-sided tape is removed, so that one surface of the top substrate, the intermediate substrate and the bottom substrate is thin-film-coated with an adhesive, or that one surface of the top substrate, the intermediate substrate and the bottom substrate is thin-film-coated with an adhesive by using a dispenser, a spray or a silk screen printing method, and then, the top substrate, the intermediate substrate and the bottom substrate are stacked and bound to each other, thereby forming the body.

17. The thin film bio valve device of claim 1, wherein the body further comprises a universal serial bus (USB) connection unit allowing the assay site to be electrically connected with a USB interface member, and thereby reading the assay site.

18. The thin film bio valve device of claim 17, wherein the electric connection between the assay site and the USB connection unit is formed by patterning an electric circuit on an aluminum thin film adhesive tape for binding the top substrate, the intermediate substrate and the bottom substrate or by patterning an electric circuit on the intermediate substrate.

19. The thin film bio valve device of claim 1, wherein the body further comprises a wireless RF IC or a solar cell for supplying power to the wireless RF IC.

20. The thin film bio valve device of claim 19, wherein the wireless RF IC further comprises a control unit for generating a control signal for an impedance measurement device or an electrochemical detection device, or a memory for storing results measured from the impedance measurement device or the electrochemical detection device.

21. The thin film bio valve device of claim 1, wherein the body comprises a material selected from the group consisting of silicon, plastic, aerogel, glass, silicon, polypropylene, polyacrylate, polyvinylalcohol, polyethylene, polymethyl methacrylate (PMMA), cyclic oleifn copolymer (COC), and polycarbonate.

22. The thin film bio valve device of claim 1, wherein the body is surface-coated with aluminum or an aluminum sheet to prevent evaporation of a liquid contained in the chamber.

23. The thin film bio valve device of claim 1, wherein the stacking and binding of the top substrate, the intermediate substrate, and the bottom substrate is performed by using an aluminum thin film adhesive tape.

24. The thin film bio valve device of claim 23, wherein the aluminum thin film adhesive tape provides a hydrophilic channel.

25. The thin film bio valve device of claim 23, wherein the aluminum thin film adhesive tape provides an electric circuit pattern for connecting semiconductor chips integrated on the body.

26. The thin film bio valve device of claim 25, wherein the electric circuit pattern comprises an interdigitated array electrode pattern, a resistance pattern for a heater, an electronic induced coil pattern, an electrode pattern for an impedance measurement device, or an electrode pattern for an electrochemical detection device.

27. An apparatus for controlling the thin film bio valve device of claim 1, comprising:
   a spindle motor for rotating the thin film bio valve device;
   a slider for moving the movable permanent magnet mounted on the slider or an actuator for moving the scan magnet mounted on the actuator; and
   a central control device for driving and controlling the spindle motor and performing space-addressing with respect to the magnetic valve,
   wherein the magnetic valve is reversibly moved vertically, in a clockwise or counter-clockwise direction, or in a radial direction, due to the attractive force between the magnetic valve and the movable permanent magnet or the attractive force between the magnetic valve and the scan magnet and thus, the channel hole is selectively opened or closed.

28. The apparatus of claim 27, wherein the space-addressing with respect to the magnetic valve comprises a radial space-addressing and an azimuth space-addressing.

29. The apparatus of claim 28, wherein the radial space-addressing is performed by moving the slider to the corresponding radius to a magnetic valve, and the azimuth space-addressing is performed by slowly rotating the spindle motor or repeatedly performing a cycle of short-rotating and stopping the spindle motor after the radial space-addressing is completed.

30. The apparatus of claim 28, wherein the azimuth space-addressing is performed by an azimuth search motor and a gear connection member.

31. The apparatus of claim 27, wherein the fluid flows by a pumping fluidic movement or a pulse valve.

32. An apparatus for controlling the thin film bio valve device of claim 1, comprising:
   a spindle motor for rotating the thin film bio valve device;
   a slider for moving the movable permanent magnet mounted on the slider, which is used to perform a radial space-addressing;
   an azimuth space-addressing member for an azimuth space-addressing and
   a central control device for driving and controlling the spindle motor and performing the radial and azimuth space-addressing with respect to the magnetic valve,
   wherein the magnetic valve is reversibly moved vertically, in a clockwise or counter-clockwise direction, or in a radial direction, due to the attractive force between the magnetic valve and the movable permanent magnet formed by the azimuth space-addressing and the radial space-addressing and thus, the channel hole is selectively opened or closed.

33. The apparatus of claim 32, wherein the azimuth space-addressing member comprises at least one selected from the group consisting of an actuator on which the scan magnet is mounted, a second slider on which the movable permanent magnet, an azimuth search motor, and a gear connection member.

34. The apparatus of claim 33, wherein the space-addressing with respect to the magnetic valve is performed by the space-addressing in the radial direction with respect to the magnetic valve and the space-addressing in the azimuth direction with respect to the magnetic valve, wherein the space-addressing in the radial direction is performed by moving in the radial direction the slider to a radius of a corresponding magnetic valve after the space-addressed in the azimuth direction is completed by the azimuth space-addressing member.

35. The apparatus of claim 33, wherein the azimuth direction is performed in such a manner that the actuator is turned to a coordinate of a spiral magnetic pattern corresponding to an azimuth to be addressed, the spindle motor is slowly turned after the second slider is moved to a radius of a corresponding magnetic valve to be addressed or a cycle of short-rotating and stopping the spindle motor is repeatedly performed after the second slider is moved to a radius of a corresponding magnetic valve to be addressed.

36. The apparatus of claim 32, further comprising a wireless radio wave generation unit for providing power to the wireless RF IC, an illuminating device for providing a light energy to the solar cell, or a USB port for providing an interface with at least one computer peripheral selected from the group consisting of a camera, a keyboard, earphones, a mouse, a memory stick, an electronic stethoscope, a sphygmomanometer, an electronic thermometer, and a pharmaceutical measuring instrument.

37. The apparatus of claim 32, wherein the central control device receives a unique ID of the thin film bio valve device transmitted from the wireless RF IC when the thin film bio valve device is loaded in the apparatus, and thereby recognizing that the thin film bio valve device currently is currently loaded in the apparatus.

38. The apparatus of claim 32, further comprising an input-output device having a communications standard of a USB, IEEE1394, ATAPI, SCSI, IDE, or a wired or wireless internet connection.

39. The apparatus of claim 32, wherein the slider further comprises an optical pick-up device.

40. The apparatus of claim 32, further comprising an optical detector that transmits a reference trigger signal to the central control device whenever the optical detector passes by a reference hole of the thin film bio valve device while the body rotates.

41. An apparatus for controlling the thin film bio valve device of claim 1, comprising:
 a spindle motor for rotating the thin film bio valve device;
 a top actuator disposed above the thin film bio valve device and a bottom actuator disposed under the thin film bio valve device, wherein the top and bottom actuators are arranged in parallel and perform space-addressing with respect to the same position, and each of the top and bottom actuators has a front end on which the scan magnet is mounted and
 a central control device for driving and controlling the spindle motor and performing space-addressing with respect to the magnetic valve,
 wherein the magnetic valve is reversibly moved vertically, in a clockwise or counter-clockwise direction, or in a radial direction, due to a combined force of attractive and repulsive forces between the magnetic valve and the scan magnets and thus, the channel hole is selectively opened or closed.

* * * * *